US009682080B2

(12) United States Patent
Su

(10) Patent No.: US 9,682,080 B2
(45) **Date of Patent: *Jun. 20, 2017**

(54) PYRUVATE KINASE ACTIVATORS FOR USE IN THERAPY

(71) Applicant: AGIOS PHARMACEUTICALS, INC, Cambridge, MA (US)

(72) Inventor: Shin-San Michael Su, Boston, MA (US)

(73) Assignee: AGIOS PHARMACEUTICALS, INC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/886,750

(22) Filed: Oct. 19, 2015

(65) Prior Publication Data

US 2016/0106742 A1 Apr. 21, 2016

Related U.S. Application Data

(63) Continuation of application No. 14/115,289, filed as application No. PCT/US2012/036412 on May 3, 2012, now Pat. No. 9,193,701.

(60) Provisional application No. 61/482,171, filed on May 3, 2011.

(51) Int. Cl.

| | |
|---|---|
| ***A61K 31/535*** | (2006.01) |
| ***C07D 413/00*** | (2006.01) |
| ***A61K 31/496*** | (2006.01) |
| ***A61K 31/4965*** | (2006.01) |
| ***A61K 31/497*** | (2006.01) |
| ***C07D 205/04*** | (2006.01) |
| ***C07D 213/81*** | (2006.01) |
| ***C07D 215/14*** | (2006.01) |
| ***C07D 235/06*** | (2006.01) |
| ***C07D 241/20*** | (2006.01) |
| ***C07D 271/12*** | (2006.01) |
| ***C07D 295/192*** | (2006.01) |
| ***C07D 333/24*** | (2006.01) |
| ***C07D 401/12*** | (2006.01) |
| ***C07D 405/12*** | (2006.01) |
| ***C07D 417/12*** | (2006.01) |

(52) U.S. Cl.

CPC .......... *A61K 31/496* (2013.01); *A61K 31/497* (2013.01); *A61K 31/4965* (2013.01); *A61K 31/535* (2013.01); *C07D 205/04* (2013.01); *C07D 213/81* (2013.01); *C07D 215/14* (2013.01); *C07D 235/06* (2013.01); *C07D 241/20* (2013.01); *C07D 271/12* (2013.01); *C07D 295/192* (2013.01); *C07D 333/24* (2013.01); *C07D 401/12* (2013.01); *C07D 405/12* (2013.01); *C07D 417/12* (2013.01)

(58) Field of Classification Search

CPC ........................... A61K 31/535; C07D 471/04

USPC ....................................... 514/234.2; 544/127

See application file for complete search history.

(56) References Cited

U.S. PATENT DOCUMENTS

| | | | | |
|---|---|---|---|---|
| 5,834,485 | A | 11/1998 | Dyke et al. | |
| 5,965,559 | A | 10/1999 | Faull et al. | |
| 5,965,569 | A | 10/1999 | Camps Garcia et al. | |
| 6,313,127 | B1 | 11/2001 | Waterson et al. | |
| 9,193,701 | B2 * | 11/2015 | Su ...................... | A61K 31/4965 |
| 2003/0095958 | A1 | 5/2003 | Bhisetti et al. | |
| 2003/0207882 | A1 | 11/2003 | Stocker et al. | |
| 2008/0214495 | A1 | 9/2008 | Alstermark et al. | |
| 2010/0331307 | A1 | 12/2010 | Salituro et al. | |
| 2014/0155408 | A1 | 6/2014 | Su | |
| 2014/0323467 | A1 | 10/2014 | Salituro et al. | |
| 2015/0183760 | A1 | 7/2015 | Salituro et al. | |

FOREIGN PATENT DOCUMENTS

| | | | |
|---|---|---|---|
| CN | 101296909 | A | 10/2008 |
| JP | 2014509458 | A | 4/2014 |
| JP | 2014509459 | A | 4/2014 |
| WO | 9630343 | A1 | 10/1996 |
| WO | 97/28128 | A1 | 8/1997 |
| WO | 97/28129 | A1 | 8/1997 |
| WO | 9744322 | A1 | 11/1997 |
| WO | 9948490 | A1 | 9/1999 |
| WO | 0119788 | A2 | 3/2001 |
| WO | 0119798 | A2 | 3/2001 |
| WO | 0164642 | A2 | 9/2001 |
| WO | 0164643 | A2 | 9/2001 |
| WO | 02100822 | A1 | 12/2002 |
| WO | 2004089470 | A2 | 10/2004 |
| WO | 2005120474 | A2 | 12/2005 |
| WO | 2006034341 | A2 | 3/2006 |
| WO | 2006-038594 | A1 | 4/2006 |
| WO | 2007003934 | A2 | 1/2007 |
| WO | 2007023186 | A1 | 3/2007 |
| WO | 2008/050168 | A1 | 5/2008 |
| WO | 2008052190 | A2 | 5/2008 |
| WO | 2008073670 | A2 | 6/2008 |
| WO | 2010130638 | A1 | 11/2010 |

(Continued)

OTHER PUBLICATIONS

Kumiko Tsujino et al., "CBA-Pk-1slc/Pk-1slcmutant mouse in Newborn period does not exhibit hemolytic anemia," Japanese Society of Animal Models for Human Diseases, 1998, vol. 14, p. 24.

Takashi Yamaoka, Adenosine deaminase hyperkinasia, Nihon Rinsho (supplementary volume) series of Syndrome for each are 20 Blood Syndrome I, Aug. 12, 1998, p. 308-311.

International Preliminary Report on Patentability for PCT/US2010/040486 dated Jan. 12, 2012.

Charache et al. "Effect of 2,3-Diphosphoglycerate on Oxygen Affinity of Blood in Sickle Cell Anemia" Journal of Clinical Investigation (1970) vol. 49, pp. 806-812.

Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.

(Continued)

*Primary Examiner* — Raymond Henley, III

(74) *Attorney, Agent, or Firm* — Lando & Anastasi, LLP

(57) ABSTRACT

Described herein are methods for using compounds that activate pyruvate kinase.

30 Claims, 58 Drawing Sheets

(56) References Cited

FOREIGN PATENT DOCUMENTS

| | | | |
|---|---|---|---|
| WO | 2011002817 | A1 | 1/2011 |
| WO | 2011032169 | A2 | 3/2011 |
| WO | 2011047432 | A1 | 4/2011 |
| WO | 2011109441 | A1 | 9/2011 |
| WO | 2012069503 | A1 | 5/2012 |
| WO | 2012/092442 | A1 | 7/2012 |
| WO | 2012151451 | A1 | 11/2012 |
| WO | 2012151452 | A1 | 11/2012 |

OTHER PUBLICATIONS

International Preliminary Report for related application No. PCT/US2011/067752 dated Apr. 11, 2013.
International Search Report and Written Opinion for International Application No. PCT/US2012/036412 dated Jul. 6, 2012.
International Search Report and Written Opinion for International Application No. PCT/US2012/036413 dated Jul. 6, 2012.
International Search Report dated Mar. 5, 2012 for related international application No. PCT/US2011/067752.
International Search Report for PCT/US10/040486 dated Sep. 1, 2010.
Pan et al. "Research Status of Pyruvate Deficiency" Chinese Journal of Hematology (1999) vol. 20, No. 4, pp. 223.
Petz et al. "Increased IgG Molecules Bound to the Surface of Red Blood Cells of Patients With Sickle Cell Anemia" Blood (1984) vol. 64, No. 1, pp. 301-304.
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-l-piperazinyl)carbonyl]phenyl]--".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazolyl)methyl]-l-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pyridinyl)-I-piperazinyl]carbonyl]phenyl]-".
STN Tokyo, Registry No. 1240875-006, entered STN on Sep. 14, 2010, Chemical Abstracts Index Name "1,4-Benzodioxin-6-sulfonamide, 2,3-dihydro-N-[4-[[4-4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-4[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3-dihydro-".
STN Tokyo, Registry No. 9200679-46-5, Entered STN on Feb. 13, 2007, Chemical Abstracts Index Name "1,4-Benzodioxin-6-sulfonamide, 2,3-dihydro-N-[4- [4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl] - 2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-l-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-l-piperazinyl)carbonyl]phenyl]-".
Supplementary Search Report for EP10794668 Mailed Oct. 18, 2012.

* cited by examiner

FIG. 1 A
| Structure | % Act. R510Q | % Act. R532W | % Act. T384W | % Act. WT | PKR WT AC50 (μM) | PKR R510Q AC50 (μM) | PKR R532W AC50 (μM) | PKR T384W AC50 (μM) | PKR G332S AC50 (μM) | PKR G364D AC50 (μM) | PKR G37E AC50 (μM) | PKR R479H AC50 (μM) |
|---|---|---|---|---|---|---|---|---|---|---|---|---|
| 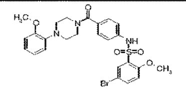 | B | B | B | B | | | | | | | | |
| 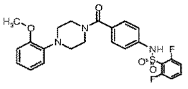 | B | B | B | B | | | | | | | | |
| 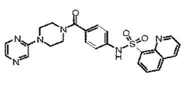 | B | B | B | B | | | | | | | | |
| 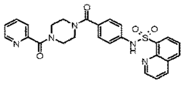 | B | B | B | B | | CC | BB | BB | | CC | | AA |
| 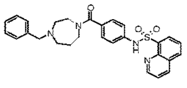 | B | B | B | B | | | | | | | | |
| 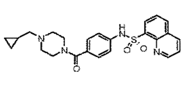 | B | B | B | B | AA | BB | AA | AA | BB | BB | CC | AA |
| 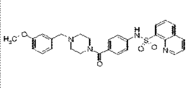 | B | B | B | B | | | | | | | | |
| 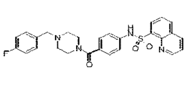 | B | B | B | B | | AA | AA | AA | | BB | | AA |
| 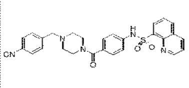 | B | B | B | B | | | | | | | | |
| 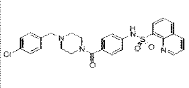 | B | B | B | B | | | | | | | | |
| 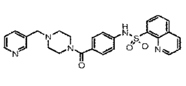 | B | B | B | B | | BB | AA | AA | AA | BB | | AA |
| 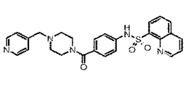 | B | B | B | B | AA | AA | AA | AA | CC | BB | | AA |
| 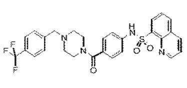 | A | A | A | B | | | | | | | | |
| 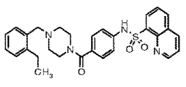 | B | B | B | B | | | | | | | | |
| 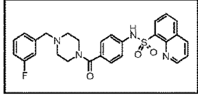 | B | B | B | B | AA | AA | AA | AA | | | | |

FIG. 1B
| | | | | | | | | | | | | |
|---|---|---|---|---|---|---|---|---|---|---|---|---|
| 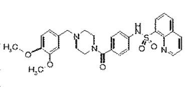 | B | B | B | B | | | | | | | | |
| 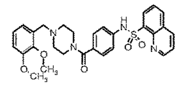 | B | B | B | B | | | | | | | | |
| 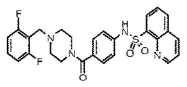 | B | B | B | B | AA | AA | AA | AA | | | | |
| 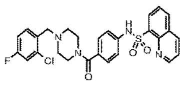 | B | B | B | B | AA | AA | AA | AA | | | | |
| 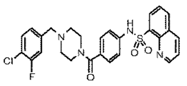 | B | B | B | B | | | | | | | | |
| 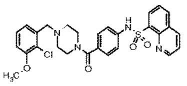 | B | B | B | B | AA | BB | AA | AA | | | | |
| 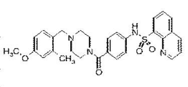 | B | B | B | B | BB | CC | AA | BB | | | | |
| 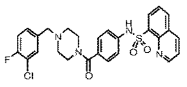 | B | B | B | B | | AA | AA | | | BB | | AA |
| 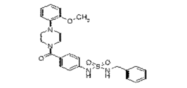 | B | B | B | B | | | | | | | | |
| 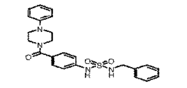 | B | B | B | B | | | | | | | | |
| 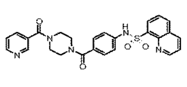 | B | B | B | B | | | | | | | | |
| 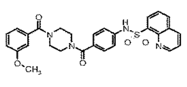 | B | B | B | B | | | | | | | | |
| 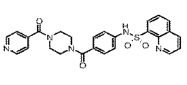 | B | B | B | A | | | | | | | | |
| 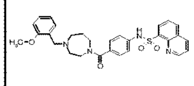 | A | B | A | B | | | | | | | | |
| 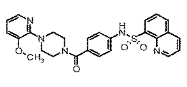 | B | B | B | B | | CC | | BB | AA | | | BB |

FIG. 1C
| | | | | | | | | | | | | |
|---|---|---|---|---|---|---|---|---|---|---|---|---|
| 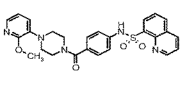 | B | B | B | A | AA | BB | AA | AA | AA | BB | | AA |
| 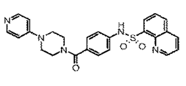 | B | B | B | B | | | | | | | | |
| 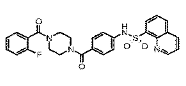 | B | B | A | A | | | | | | | | |
| 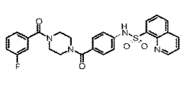 | B | B | B | B | | | | | | | | |
| 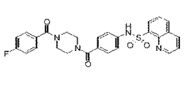 | A | A | A | A | | | | | | | | |
| 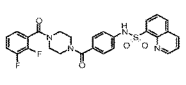 | B | B | B | B | | | | | AA | BB | | AA |
| 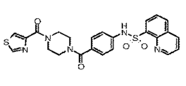 | B | A | A | A | | CC | CC | | | CC | | CC |
| 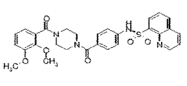 | B | B | A | B | | | | | | | | |
| 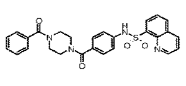 | B | A | A | A | | | | | | | | |
| 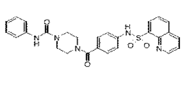 | B | B | B | B | | | | | | | | |
| 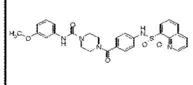 | B | B | A | A | | | | | | | | |
| 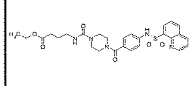 | A | B | A | B | | | | | | | | |
| 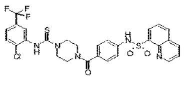 | A | B | B | B | | | | | | | | |
| 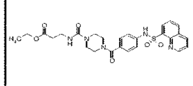 | B | B | B | B | | | | | | | | |
| 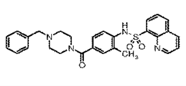 | B | A | B | B | | | | | | | | |

FIG. 1D
| | | | | | | | | | | | | |
|---|---|---|---|---|---|---|---|---|---|---|---|---|
| 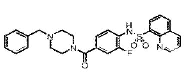 | B | A | B | A | | | | | | | | |
| 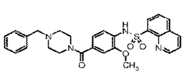 | B | B | A | A | | | | | | | | |
| 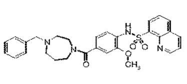 | B | A | B | A | | | | | | | | |
| 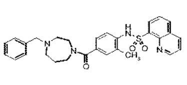 | B | A | A | A | | | | | | | | |
| 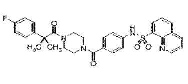 | B | A | B | A | | | | | | | | |
| 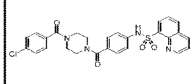 | B | B | B | B | | | | | | | | |
| 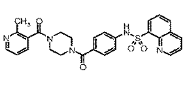 | B | B | B | B | | | | | | | | |
| 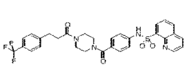 | B | B | B | B | | | | | | | | |
| 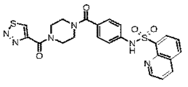 | B | B | B | B | | | | | | | | |
| 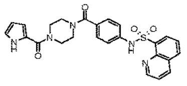 | B | B | A | B | | | | | | | | |
| 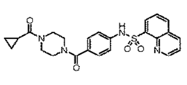 | A | A | A | A | | | | | | | | |
| 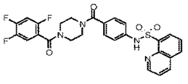 | B | B | B | B | | | | | | | | |
| 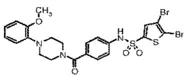 | B | B | A | A | | | | | | | | |
| 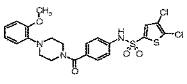 | B | B | B | B | | | | | | | | |
| 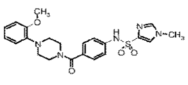 | A | B | A | A | | | | | | | | |

FIG. 1E
| | | | | | | | | | | | | |
|---|---|---|---|---|---|---|---|---|---|---|---|---|
| 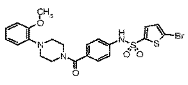 | B | B | B | B | | | | | | | | |
| 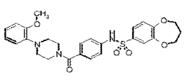 | B | B | B | B | | | | | | | | |
| 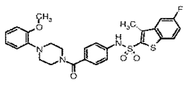 | B | B | B | B | | | | | | | | |
| 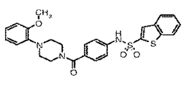 | B | A | A | A | | | | | | | | |
| 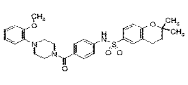 | B | B | B | B | | | | | | | | |
| 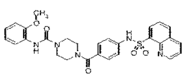 | B | B | B | B | | | | | | | | |
| 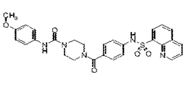 | A | B | B | A | | | | | | | | |
| 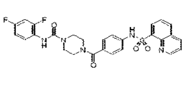 | B | B | B | B | | | | | | | | |
| 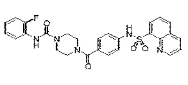 | B | B | B | B | | | | | | | | |
| 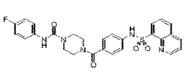 | B | B | B | B | | | | | | | | |
| 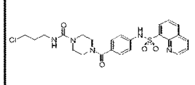 | B | B | B | B | | | | | | | | |
| 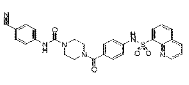 | B | B | B | B | | | | | | | | |
| 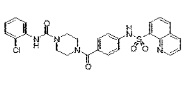 | B | A | A | A | | | | | | | | |
| 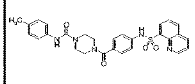 | B | A | A | A | | | | | | | | |
| 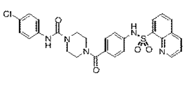 | B | A | A | A | | | | | | | | |

FIG. 1E
| | | | | | | | | | | | | |
|---|---|---|---|---|---|---|---|---|---|---|---|---|
| 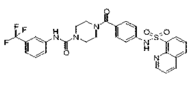 | B | A | A | A | | | | | | | | |
| 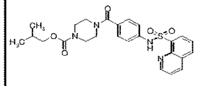 | B | A | A | A | | CC | BB | BB | BB | CC | | BB |
| 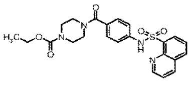 | B | A | A | A | | | | | | | | |
| 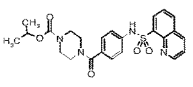 | B | A | A | A | | CC | AA | BB | CC | CC | CC | BB |
| 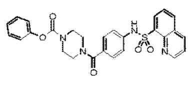 | B | B | B | B | | | | | | | | |
| 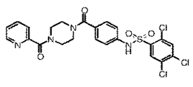 | B | B | B | B | | | | | | | | |
| 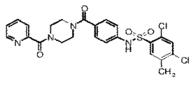 | B | B | B | B | | | | | | | | |
| 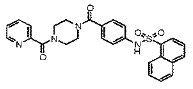 | B | B | B | B | | | | | | | | |
| 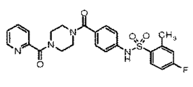 | B | B | B | B | | | | | | | | |
| 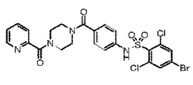 | A | B | B | B | | | | | | | | |
| 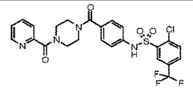 | B | B | B | B | | | | | | | | |
| 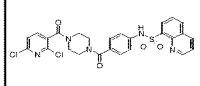 | A | B | B | B | | | | | | | | |
| 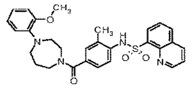 | B | A | A | A | | | | | | | | |
| 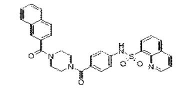 | B | A | B | B | | | | | | | | |
| 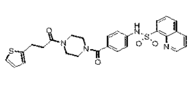 | A | B | B | B | | | | | | | | |

FIG. 1G
| | | | | | | | | | | | | |
|---|---|---|---|---|---|---|---|---|---|---|---|---|
| 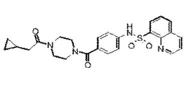 | B | B | B | B | | | | | | | | |
| 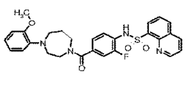 | B | B | B | B | | | | | | | | |
| 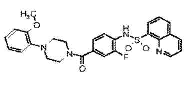 | A | A | B | B | | | | | | | | |
| 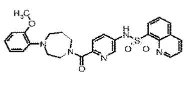 | B | A | B | B | | | | | | | | |
| 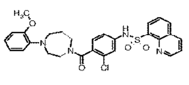 | A | B | B | B | | | | | | | | |
| 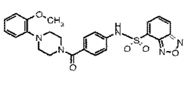 | A | B | B | A | | | | | | | | |
| 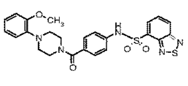 | B | B | B | B | | | | | | | | |
| 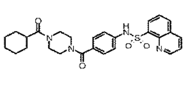 | B | B | B | B | | | | | | | | |
| 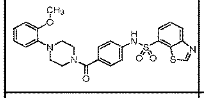 | A | B | A | A | AA | BB | AA | AA | | | | |
| 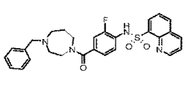 | B | B | B | A | | | | | | | | |
| 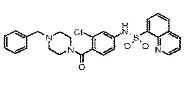 | B | B | B | B | | | | | | | | |
| 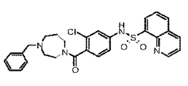 | B | C | B | B | | | | | | | | |
| 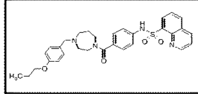 | B | B | B | B | | CC | CC | | | | | |
| 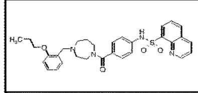 | B | B | B | B | | | | | | | | |
| 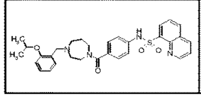 | B | B | B | B | | | | | | | | |

FIG. 1H
| | | | | | | | | | | | |
|---|---|---|---|---|---|---|---|---|---|---|---|
| 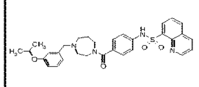 | B | B | B | B | CC | | CC | | | | |
| 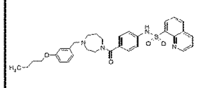 | B | B | B | B | | | | | | | |
| 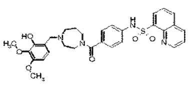 | B | B | B | B | | | | | | | |
| 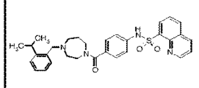 | A | B | B | B | | | | | | | |
| 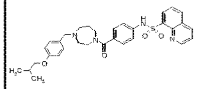 | B | B | B | B | | | | | | | |
| 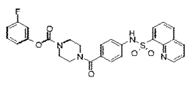 | B | B | B | B | | | | | | | |
| 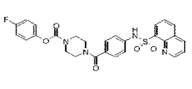 | B | B | B | B | | | | | | | |
| 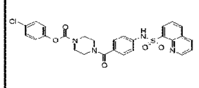 | B | B | A | B | | | | | | | |
| 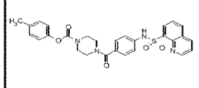 | B | B | B | B | | | | | | | |
| 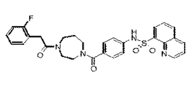 | B | B | B | B | | | | | | | |
| 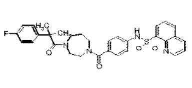 | B | B | B | B | | | | | | | |
| 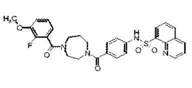 | A | A | B | A | | | | | | | |
| 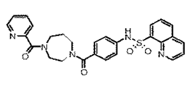 | A | A | A | B | | | | | | | |
| 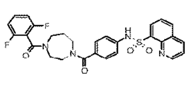 | A | B | B | A | | | | | | | |
| 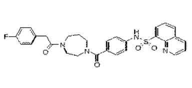 | A | B | B | B | | | | | | | |

FIG. 1I
| | | | | | | | | | | | | |
|---|---|---|---|---|---|---|---|---|---|---|---|---|
| 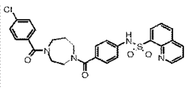 | B | B | B | B | | | | | | | | |
| 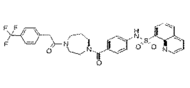 | B | B | B | B | | | | | | | | |
| 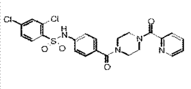 | B | B | A | B | | | | | | | | |
| 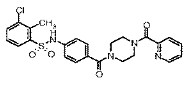 | A | A | B | A | | | | | | | | |
| 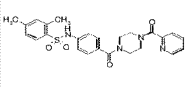 | A | B | B | A | | | | | | | | |
| 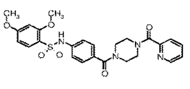 | A | B | B | B | | | | | | | | |
| 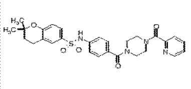 | B | B | B | A | | | | | | | | |
| 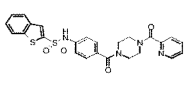 | B | B | B | B | | | | | | | | |
| 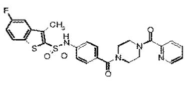 | B | B | A | B | | | | | | | | |
| 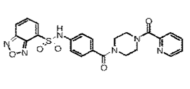 | B | B | B | B | | | | | | | | |
| 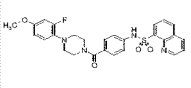 | B | A | B | B | | | | | | | | |
| 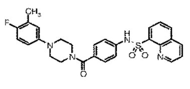 | B | B | B | B | | | | | | | | |
| 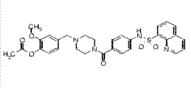 | B | B | B | B | CC | CC | BB | | | | | |
| 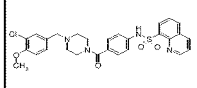 | B | B | B | B | BB | CC | BB | BB | | | | |
| 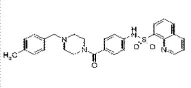 | B | B | B | B | | | | | | | | |

FIG. 1J
| | | | | | | | | | | | | |
|---|---|---|---|---|---|---|---|---|---|---|---|---|
| 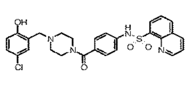 | A | A | B | A | | | | | | | | |
| 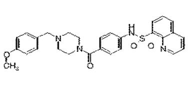 | A | B | B | B | | | | | | | | |
| 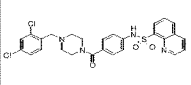 | B | A | B | A | | | | | | | | |
| 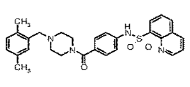 | A | B | B | B | | | | | | | | |
| 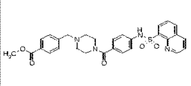 | B | A | B | A | | | | | | | | |
| 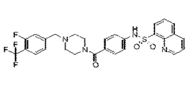 | B | B | B | B | | | | | | | | |
| 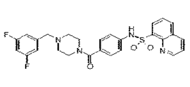 | B | B | B | B | | AA | AA | AA | | BB | | AA |
| 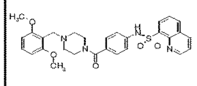 | B | B | B | B | | | | | | | | |
| 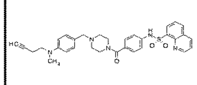 | B | B | B | B | CC | CC | CC | CC | | | | |
| 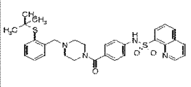 | B | B | B | B | BB | CC | BB | BB | | | | |
| 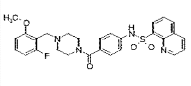 | B | B | B | B | AA | AA | AA | AA | | | | |
| 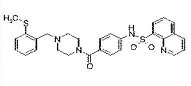 | B | B | B | B | AA | AA | AA | AA | | | | |
| 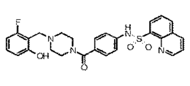 | B | B | B | B | AA | AA | AA | | | | | |
| 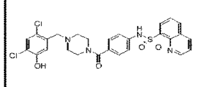 | B | B | B | B | AA | CC | | | | | | |
| 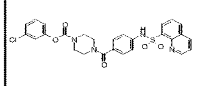 | B | B | B | B | | | | | | | | |

FIG. 1K
| | | | | | | | | | | | | |
|---|---|---|---|---|---|---|---|---|---|---|---|---|
| 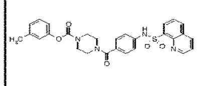 | B | B | B | B | | | | | | | | |
| 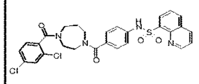 | A | B | B | B | | | | | | | | |
| 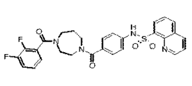 | B | B | B | B | | | | | | | | |
| 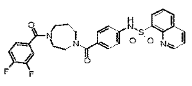 | B | B | B | B | | | | | | | | |
| 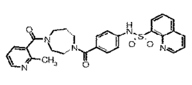 | B | B | B | B | | | | | | | | |
| 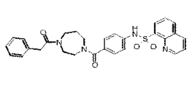 | B | B | B | B | | | | | | | | |
| 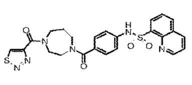 | A | B | B | B | | | | | | | | |
| 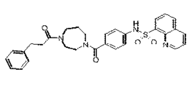 | B | B | B | B | | | | | | | | |
| 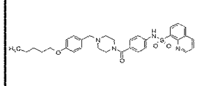 | B | B | B | A | | | | | | | | |
| 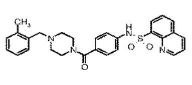 | B | B | B | B | | | | | | | | |
| 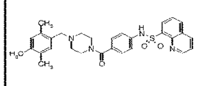 | B | B | A | A | | | | | | | | |
| 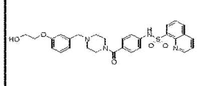 | B | B | A | A | | | | | | | | |
| 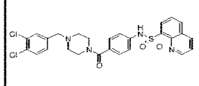 | A | B | A | A | | | | | | | | |
| 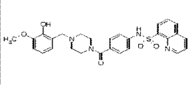 | B | B | A | A | | | | | | | | |
| 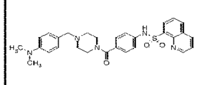 | B | B | B | B | CC | CC | CC | CC | | | | |

FIG. 1L
| | | | | | | | | | | | | |
|---|---|---|---|---|---|---|---|---|---|---|---|---|
| 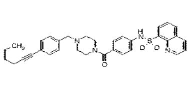 | B | B | B | B | | | | | | | | |
| 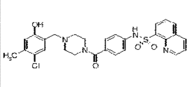 | B | B | B | B | CC | CC | BB | | | | | |
| 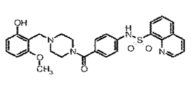 | B | B | B | B | | | | | | | | |
| 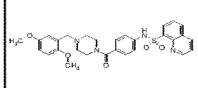 | B | B | B | B | | | | | | | | |
| 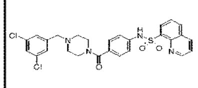 | B | B | B | B | | | | | | | | |
| 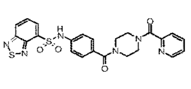 | B | B | B | B | | | | | | | | |
| 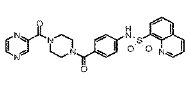 | B | B | B | B | CC | | | | | | | |
| 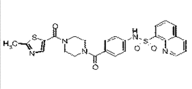 | B | B | B | B | | | | | | | | |
| 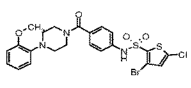 | B | B | B | B | | | | | | | | |
| 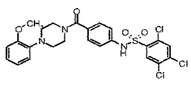 | B | B | B | B | | | | | | | | |
| 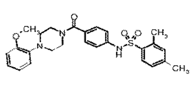 | B | B | B | B | | | | | | | | |
| 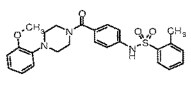 | B | B | B | B | | | | | | | | |
| 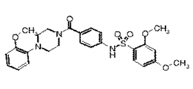 | B | B | B | B | | | | | | | | |
| 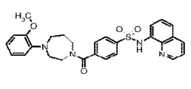 | B | B | B | B | | | | | | | | |
| 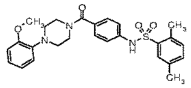 | B | B | B | B | | | | | | | | |

FIG. 1 M
| | | | | | | | | | | | | |
|---|---|---|---|---|---|---|---|---|---|---|---|---|
| 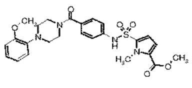 | B | B | B | B | | | | | | | | |
| 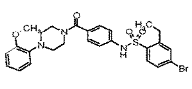 | A | B | B | B | | | | | | | | |
| 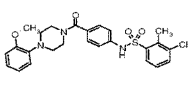 | B | A | B | A | | | | | | | | |
| 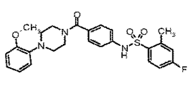 | B | B | B | B | | | | | | | | |
| 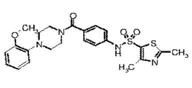 | B | B | A | A | | | | | | | | |
| 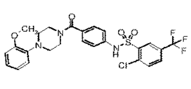 | B | B | B | B | | | | | | | | |
| 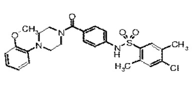 | B | B | B | B | | | | | | | | |
| 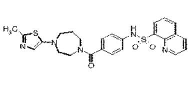 | B | B | B | B | | | | | | | | |
| 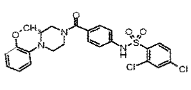 | B | B | B | B | | | | | | | | |
| 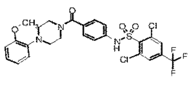 | B | B | B | B | | | | | | | | |
| 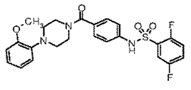 | B | B | B | B | | | | | | | | |
| 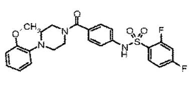 | A | B | B | B | | | | | | | | |
| 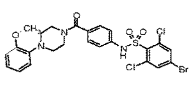 | B | B | B | B | | | | | | | | |
| 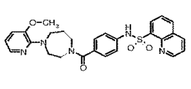 | B | B | B | B | | CC | | | | | | |
| 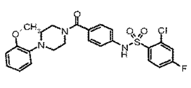 | B | B | B | B | | | | | | | | |

FIG. 1N
| | | | | | | | | | | | | |
|---|---|---|---|---|---|---|---|---|---|---|---|---|
| 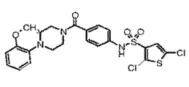 | B | B | B | B | | | | | | | | |
| 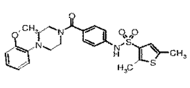 | B | B | B | B | | | | | | | | |
| 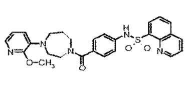 | A | B | B | B | | | | | | | | |
| 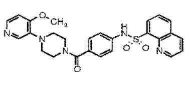 | B | B | B | B | BB | CC | CC | CC | | | | |
| 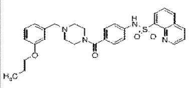 | B | A | B | B | | | | | | | | |
| 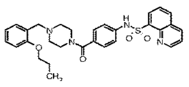 | B | B | B | B | AA | BB | AA | | | | | |
| 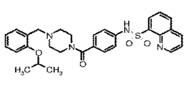 | A | A | B | A | | | | | | | | |
| 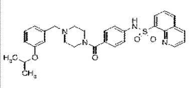 | B | B | B | B | AA | CC | AA | AA | | | | |
| 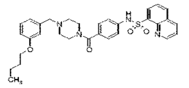 | B | B | B | B | BB | CC | AA | BB | | | | |
| 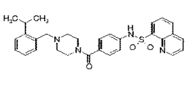 | B | B | B | B | | | | | | | | |
| 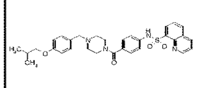 | B | A | A | A | | | | | | | | |
| 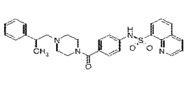 | B | B | B | B | AA | BB | AA | AA | | | | |
| 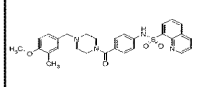 | B | B | B | B | BB | CC | BB | BB | | | | |
| 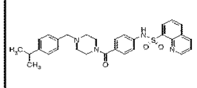 | B | B | B | B | CC | CC | BB | BB | | | | |
| 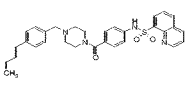 | B | B | B | B | | | | | | | | |

FIG. 1O
| | | | | | | | | | | | | |
|---|---|---|---|---|---|---|---|---|---|---|---|---|
| 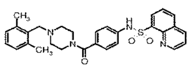 | B | B | B | B | | CC | | | | | | |
| 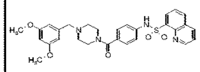 | B | B | B | B | CC | CC | BB | | | | | |
| 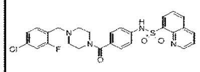 | B | B | B | B | | | | | | | | |
| 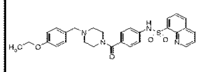 | B | B | B | B | | | | | | | | |
| 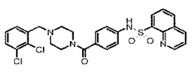 | B | B | B | B | AA | AA | AA | | | | | |
| 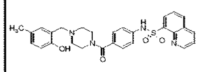 | B | B | B | B | AA | AA | | | | | | |
| 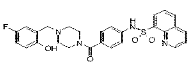 | B | B | B | B | AA | AA | AA | AA | | | | |
| 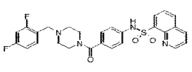 | B | B | C | B | AA | AA | | | | | | |
| 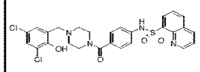 | B | B | B | B | AA | CC | | | | | | |
| 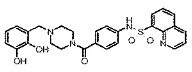 | B | B | B | B | AA | AA | | AA | | | | |
| 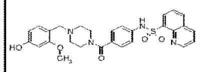 | B | B | B | B | AA | BB | AA | AA | | | | |
| 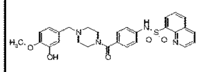 | B | B | B | B | | CC | AA | | | | | |
| 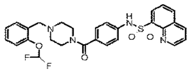 | B | B | B | B | | | | | | | | |
| 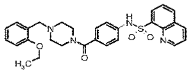 | B | B | A | B | AA | BB | AA | AA | | | | |
| 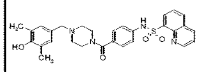 | B | B | B | B | | | | | | | | |

FIG. 1P
| | | | | | | | | | | | | |
|---|---|---|---|---|---|---|---|---|---|---|---|---|
| 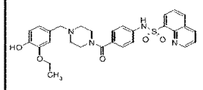 | B | B | B | B | AA | CC | | | | | | |
| 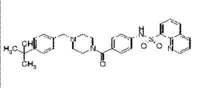 | B | B | B | B | | | | | | | | |
| 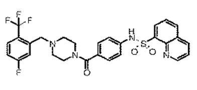 | B | B | B | B | | | | | | | | |
| 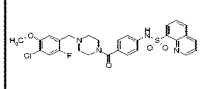 | B | B | B | B | | | | | | | | |
| 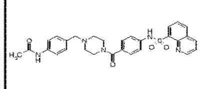 | B | B | B | B | | | | | | | | |
| 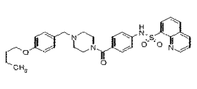 | B | B | B | B | | | | | | | | |
| 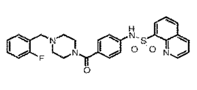 | B | B | A | B | | | | | | | | |
| 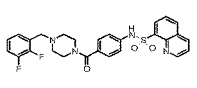 | B | B | B | B | | | | | | | | |
| 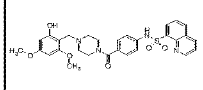 | B | B | A | A | | | | | | | | |
| 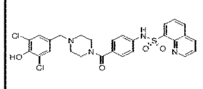 | B | B | B | B | AA | CC | AA | AA | | | | |
| 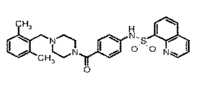 | B | B | B | B | | | | | | | | |
| 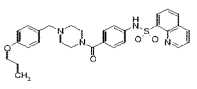 | B | B | B | B | | | | | | | | |
| 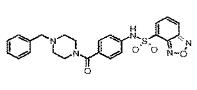 | B | B | B | B | | | | | | | | |
| 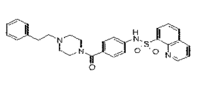 | A | A | B | B | | | | | | | | |
| 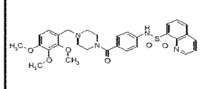 | B | B | B | B | | | | | | | | |

FIG. 1Q
| | | | | | | | | | | | |
|---|---|---|---|---|---|---|---|---|---|---|---|
| 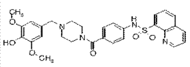 | B | A | B | B | | | | | | | |
| 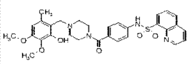 | B | A | A | B | | | | | | | |
| 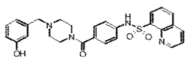 | B | A | A | B | | | | | | | |
| 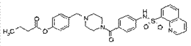 | B | B | B | B | | | | | | | |
| 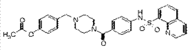 | B | B | A | B | | | | | | | |
| 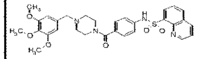 | A | A | A | B | | | | | | | |
| 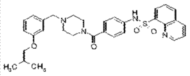 | A | A | A | B | | | | | | | |
| 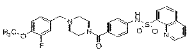 | B | A | B | B | | | | | | | |
| 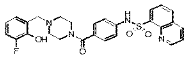 | A | A | B | B | | | | | | | |
| 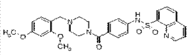 | A | A | A | B | | | | | | | |
| 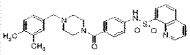 | B | B | B | B | | | | | | | |
| 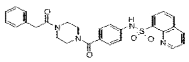 | B | B | A | B | | | | | | | |
| 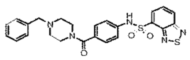 | B | B | A | B | | | | | | | |
| 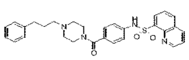 | B | B | B | B | | | | | | | |
| 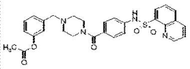 | B | B | B | B | | | | | | | |

FIG. 1R
| | | | | | | | | | | | |
|---|---|---|---|---|---|---|---|---|---|---|---|
| 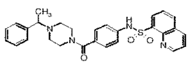 | B | B | B | B | | | | | | | |
| 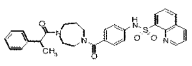 | B | B | B | B | | | | | | | |
| 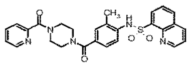 | B | A | B | B | | BB | | | | | |
| 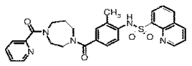 | B | B | B | B | | | | | | | |
| 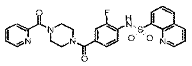 | B | B | B | B | | | | | | | |
| 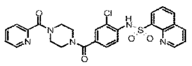 | B | A | B | B | | | | | | | |
| 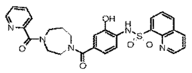 | B | A | A | B | | | | | | | |
| 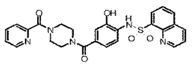 | B | A | B | B | | | | | | | |
| 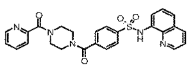 | B | B | B | B | | | | | | | |
| 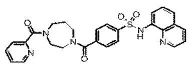 | B | A | B | B | | | | | | | |
| 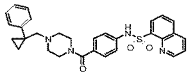 | B | B | B | B | | | | | | | |
| 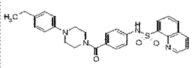 | B | B | B | B | | | | | | | |
| 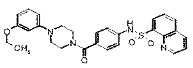 | B | B | B | B | | | | | | | |
| 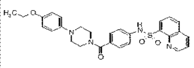 | B | A | B | B | | | | | | | |
| 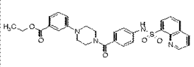 | B | A | B | B | | | | | | | |

FIG. 1S
| | | | | | | | | | | | |
|---|---|---|---|---|---|---|---|---|---|---|---|
| 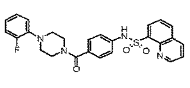 | B | B | B | B | | | | | | | |
| 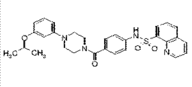 | B | A | B | B | | | | | | | |
| 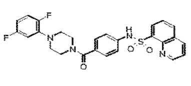 | B | A | B | A | | | | | | | |
| 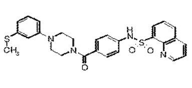 | B | B | B | B | | | | | | | |
| 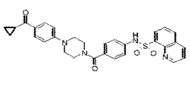 | B | B | B | B | | | | | | | |
| 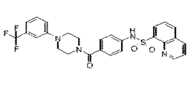 | B | B | B | B | | | | | | | |
| 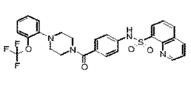 | B | B | B | B | AA | BB | AA | AA | | | |
| 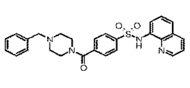 | B | B | B | B | | | | | | | |
| 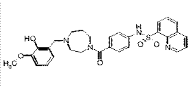 | B | A | B | B | | | | | | | |
| 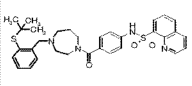 | B | A | B | B | | | | | | | |
| 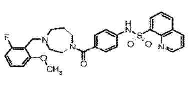 | B | A | B | B | | | | | | | |
| 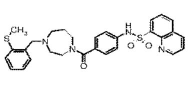 | B | A | B | B | | | | | | | |
| 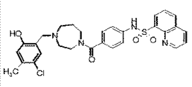 | B | A | B | B | | | | | | | |
| 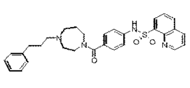 | B | A | B | B | | | | | | | |
| 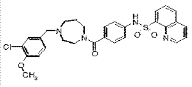 | B | B | B | B | | | | | | | |

FIG. 1I
| | | | | | | | | | | | | |
|---|---|---|---|---|---|---|---|---|---|---|---|---|
| 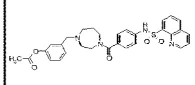 | B | B | B | B | | | | | | | | |
| 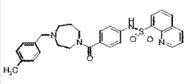 | B | B | B | B | | | | | | | | |
| 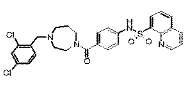 | B | B | A | B | | | | | | | | |
| 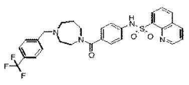 | B | B | B | B | | | | | | | | |
| 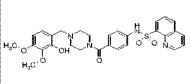 | B | B | A | B | | | | | | | | |
| 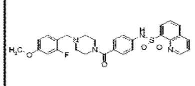 | B | B | A | B | | | | | | | | |
| 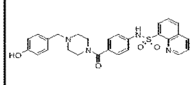 | B | B | B | B | | | | | | | | |
| 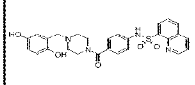 | B | B | B | B | | | | | | | | |
| 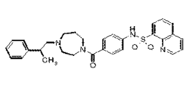 | A | A | B | B | | | | | | | | |
| 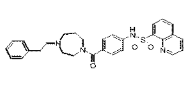 | B | A | B | A | | | | | | | | |
| 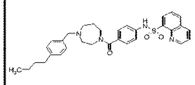 | A | B | B | B | | | | | | | | |
| 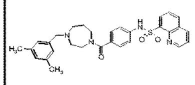 | B | B | B | B | | | | | | | | |
| 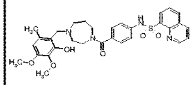 | B | A | B | B | | | | | | | | |
| 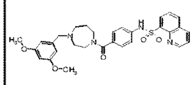 | B | B | B | B | | | | | | | | |
| 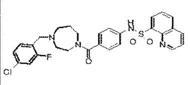 | B | B | B | B | | | | | | | | |

FIG. 1U
| | | | | | | | | | | | |
|---|---|---|---|---|---|---|---|---|---|---|---|
| 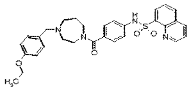 | B | B | B | B | | | | | | | |
| 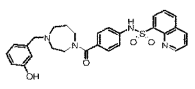 | B | B | B | B | | | | | | | |
| 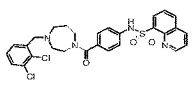 | B | B | B | B | | CC | | | | | |
| 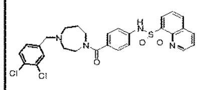 | B | B | B | B | | | | | | | |
| 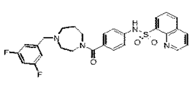 | B | B | B | B | | | | | | | |
| 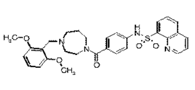 | A | A | A | A | | | | | | | |
| 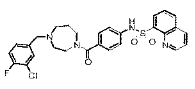 | A | A | A | A | | | | | | | |
| 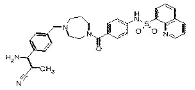 | B | B | B | B | | | | | | | |
| 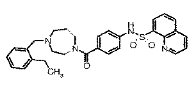 | B | A | A | A | | | | | | | |
| 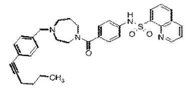 | B | A | A | A | | | | | | | |
| 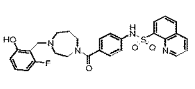 | B | B | A | B | | | | | | | |
| 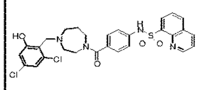 | B | A | A | A | | | | | | | |
| 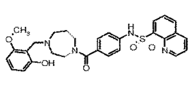 | B | B | B | B | | | | | | | |
| 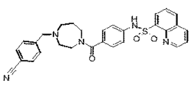 | B | A | A | A | | | | | | | |
| 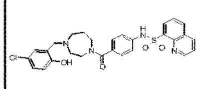 | B | A | A | A | | | | | | | |

FIG. 1V
| | | | | | | | | | | | | |
|---|---|---|---|---|---|---|---|---|---|---|---|---|
| 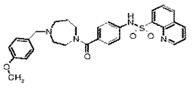 | B | A | A | A | | | | | | | | |
| 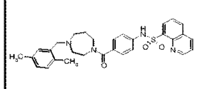 | B | A | A | B | | | | | | | | |
| 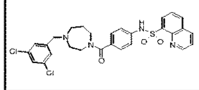 | A | A | B | A | | | | | | | | |
| 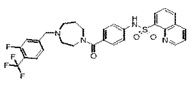 | B | A | A | B | | | | | | | | |
| 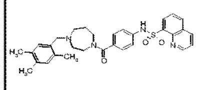 | B | B | B | A | | | | | | | | |
| 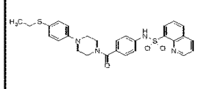 | A | A | A | A | | | | | | | | |
| 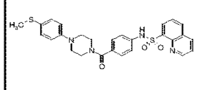 | B | B | A | A | | | | | | | | |
| 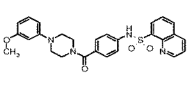 | A | A | A | A | | | | | | | | |
| 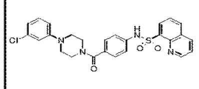 | A | A | A | A | | | | | | | | |
| 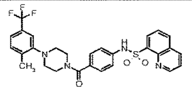 | B | B | B | B | | | | | | | | |
| 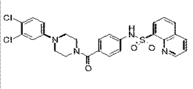 | A | A | A | A | | | | | | | | |
| 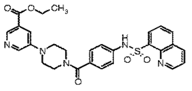 | B | B | B | A | | | | | | | | |
| 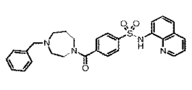 | B | A | B | B | | | | | | | | |
| 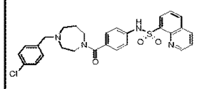 | B | A | B | B | | | | | | | | |
| 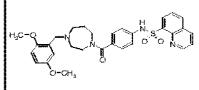 | B | A | B | B | | | | | | | | |

FIG. 1W
| | | | | | | | | | | | |
|---|---|---|---|---|---|---|---|---|---|---|---|
| 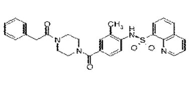 | B | A | B | B | | | | | | | |
| 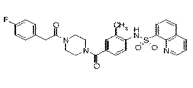 | B | A | A | B | | | | | | | |
| 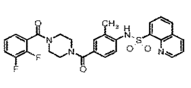 | B | A | B | B | | | | | | | |
| 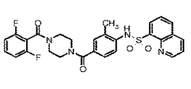 | B | B | A | B | | | | | | | |
| 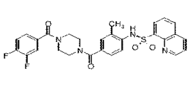 | B | A | A | B | | | | | | | |
| 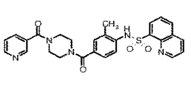 | A | A | A | B | | | | | | | |
| 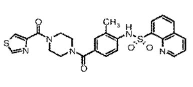 | B | B | B | B | | | | | | | |
| 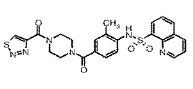 | B | B | B | B | | | | | | | |
| 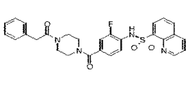 | B | B | B | B | | | | | | | |
| 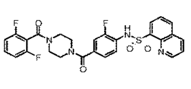 | B | A | A | A | | | | | | | |
| 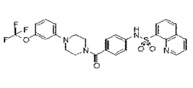 | B | A | A | B | | | | | | | |
| 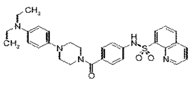 | B | A | B | B | | | | | | | |
| 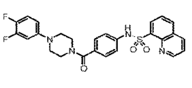 | B | A | B | B | | | | | | | |
| 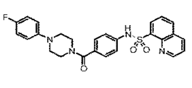 | B | A | B | B | | | | | | | |
| 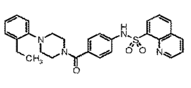 | B | B | B | B | | | | | | | |

FIG. 1X
| | | | | | | | | | | | |
|---|---|---|---|---|---|---|---|---|---|---|---|
| 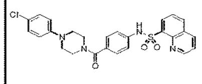 | B | A | B | B | | | | | | | |
| 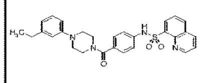 | A | A | A | B | | | | | | | |
| 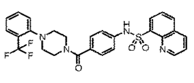 | B | A | B | B | AA | BB | AA | AA | | | |
| 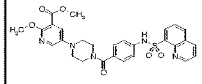 | B | A | B | B | | | | | | | |
| 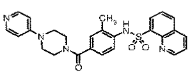 | B | B | B | B | | | | | | | |
| 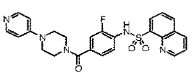 | B | B | B | B | | | | | | | |
| 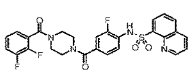 | A | A | A | B | | | | | | | |
| 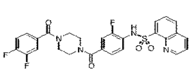 | B | B | A | B | | | | | | | |
| 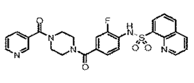 | B | B | B | B | | | | | | | |
| 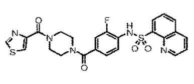 | B | B | B | B | | | | | | | |
| 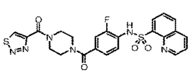 | B | B | B | B | | | | | | | |
| 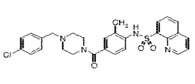 | B | B | B | B | AA | AA | | | | | |
| 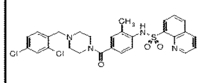 | B | A | A | A | | | | | | | |
| 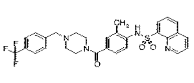 | B | B | B | B | | | | | | | |
| 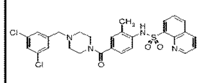 | B | B | B | B | AA | BB | AA | | | | |

FIG. 1Y
| | | | | | | | | | | | | |
|---|---|---|---|---|---|---|---|---|---|---|---|---|
| 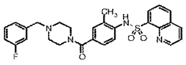 | B | B | A | B | | | | | | | | |
| 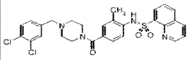 | B | A | A | B | | | | | | | | |
| 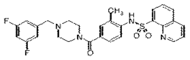 | B | A | A | A | | | | | | | | |
| 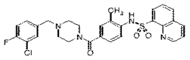 | B | B | B | B | | | | | | | | |
| 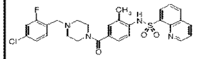 | B | B | A | B | | | | | | | | |
| 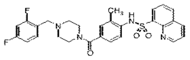 | B | B | B | B | | | | | | | | |
| 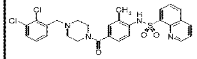 | B | B | B | B | | | | | | | | |
| 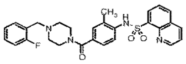 | B | B | B | B | | | | | | | | |
| 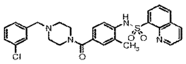 | B | B | B | B | | | | | | | | |
| 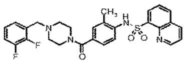 | B | B | B | B | | | | | | | | |
| 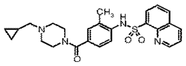 | B | B | B | B | | | | | | | | |
| 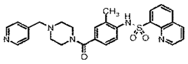 | B | B | A | B | | | | | | | | |
| 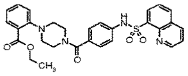 | B | B | B | B | AA | CC | AA | AA | | BB | | AA |
| 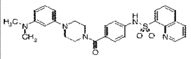 | B | B | B | B | | | | | | | | |
| 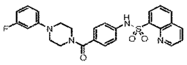 | B | A | B | B | | | | | | | | |

FIG. 1Z
| | | | | | | | | | | | | |
|---|---|---|---|---|---|---|---|---|---|---|---|---|
| 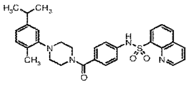 | B | A | B | B | | | | | | | | |
| 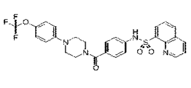 | B | A | B | B | | | | | | | | |
| 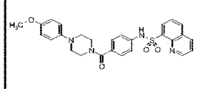 | B | A | B | B | | | | | | | | |
| 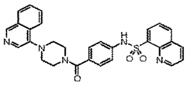 | B | B | B | B | | | | | | | | |
| 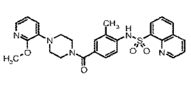 | B | B | B | B | AA | BB | AA | AA | | | | |
| 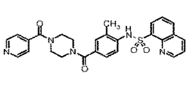 | B | A | B | B | | | | | | | | |
| 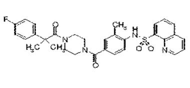 | B | A | B | B | | | | | | | | |
| 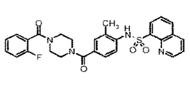 | B | B | B | B | | | | | | | | |
| 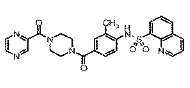 | B | A | B | B | | | | | | | | |
| 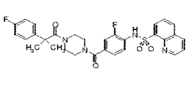 | B | A | A | A | | | | | | | | |
| 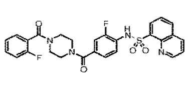 | A | B | B | A | | | | | | | | |
| 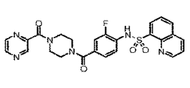 | B | B | A | B | | | | | | | | |
| 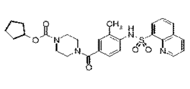 | A | A | A | B | | | | | | | | |
| 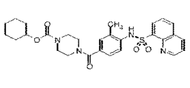 | B | B | A | B | | | | | | | | |
| 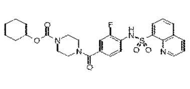 | B | A | B | B | | | | | | | | |

FIG. 1 AA
| | | | | | | | | | | | | |
|---|---|---|---|---|---|---|---|---|---|---|---|---|
| 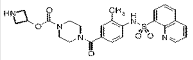 | B | A | B | B | | | | | | | | |
| 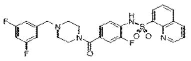 | B | A | B | B | | | | | | | | |
| 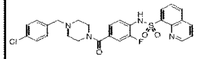 | B | B | A | B | | | | | | | | |
| 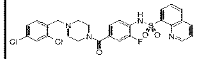 | B | B | B | B | | | | | | | | |
| 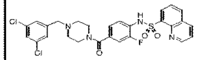 | B | A | A | B | | | | | | | | |
| 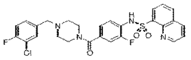 | B | B | B | B | | | | | | | | |
| 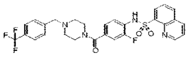 | B | B | B | B | | | | | | | | |
| 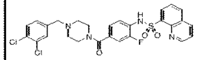 | B | B | B | B | | | | | | | | |
| 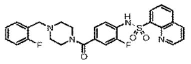 | B | B | B | B | | | | | | | | |
| 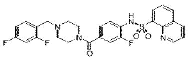 | B | B | B | B | | | | | | | | |
| 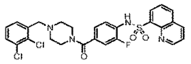 | B | B | B | B | | | | | | | | |
| 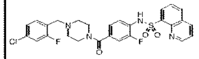 | B | B | B | B | | | | | | | | |
| 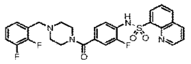 | B | B | B | B | | | | | | | | |
| 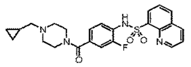 | B | B | B | B | | | | | | | | |
| 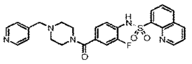 | B | B | B | B | | | | | | | | |

FIG. 1BB
| | | | | | | | | | | | | |
|---|---|---|---|---|---|---|---|---|---|---|---|---|
| 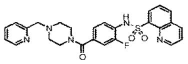 | B | B | B | B | | | | | | | | |
| 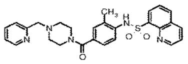 | B | B | B | B | | | | | | | | |
| 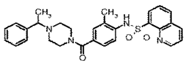 | B | B | B | B | | | | | | | | |
| 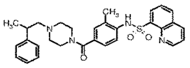 | B | B | B | B | | | | | | | | |
| 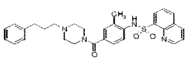 | B | B | B | B | | | | | | | | |
| 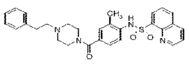 | B | B | B | B | | | | | | | | |
| 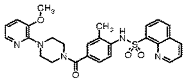 | B | A | B | B | AA | CC | AA | AA | | | | |
| 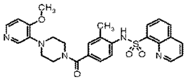 | B | A | A | B | BB | CC | BB | BB | | | | |
| 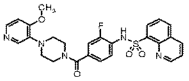 | B | B | B | B | CC | CC | CC | CC | | | | |
| 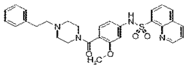 | B | B | A | B | | | | | | | | |
| 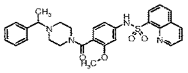 | B | A | A | B | | | | | | | | |
| 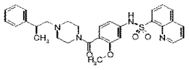 | A | A | A | B | | | | | | | | |
| 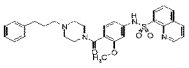 | B | A | B | B | | | | | | | | |
| 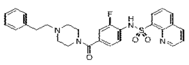 | B | A | B | B | | | | | | | | |
| 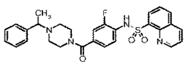 | B | B | B | B | | | | | | | | |

FIG. 1CC
| | | | | | | | | | | | |
|---|---|---|---|---|---|---|---|---|---|---|---|
| 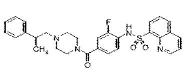 | A | B | B | B | | | | | | | |
| 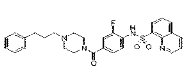 | B | B | B | A | | | | | | | |
| 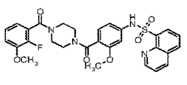 | B | A | A | A | | | | | | | |
| 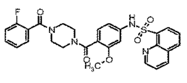 | A | B | B | B | | | | | | | |
| 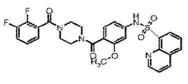 | B | B | B | B | | | | | | | |
| 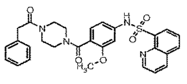 | B | B | B | B | | | | | | | |
| 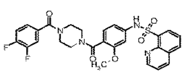 | B | B | B | B | | | | | | | |
| 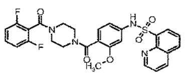 | B | B | B | B | | | | | | | |
| 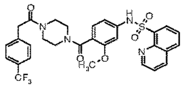 | B | B | B | B | | | | | | | |
| 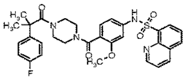 | B | B | B | B | | | | | | | |
| 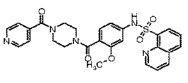 | B | B | B | B | | | | | | | |
| 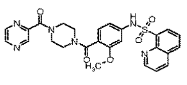 | B | B | B | B | | | | | | | |
| 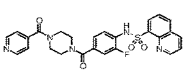 | B | B | B | B | | | | | | | |
| 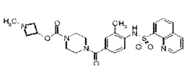 | A | A | B | B | | | | | | | |
| 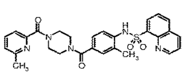 | B | B | B | B | | | | | | | |

FIG. 1 DD
| | | | | | | | | | | | | |
|---|---|---|---|---|---|---|---|---|---|---|---|---|
| 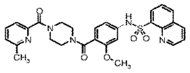 | A | A | B | B | | | | | | | | |
| 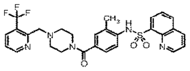 | B | B | B | B | | | | | | | | |
| 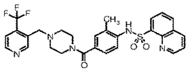 | B | B | B | B | | | | | | | | |
| 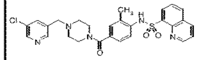 | B | B | B | B | | | | | | | | |
| 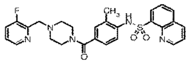 | B | B | B | B | | | | | | | | |
| 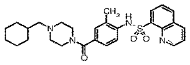 | B | A | B | B | | | | | | | | |
| 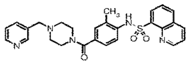 | B | B | B | B | | | | | | | | |
| 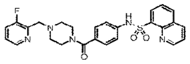 | B | B | B | B | | | | | | | | |
| 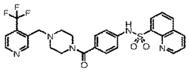 | B | B | B | B | | | | | | | | |
| 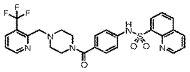 | B | B | B | B | | | | | | | | |
| 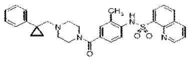 | B | B | B | B | | | | | | | | |
| 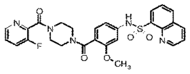 | B | B | B | B | AA | BB | | | | CC | | AA |
| 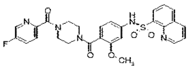 | B | B | B | B | | | | | | | | |
| 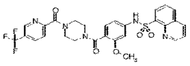 | B | B | B | B | BB | CC | BB | | | | | |
| 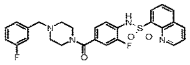 | B | B | B | B | | | | | | | | |

FIG. 1 EE
| | | | | | | | | | | | | |
|---|---|---|---|---|---|---|---|---|---|---|---|---|
| 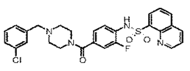 | B | B | B | B | | | | | | | | |
| 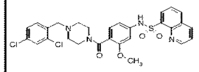 | B | B | B | A | | | | | | | | |
| 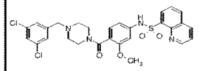 | B | B | A | B | | | | | | | | |
| 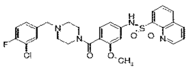 | B | A | B | B | | | | | | | | |
| 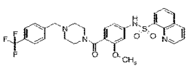 | A | A | A | A | | | | | | | | |
| 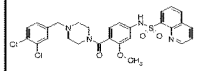 | A | B | B | B | | | | | | | | |
| 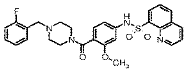 | A | A | B | B | | | | | | | | |
| 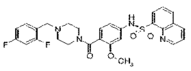 | B | B | B | B | | | | | | | | |
| 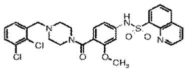 | B | B | B | B | | | | | | | | |
| 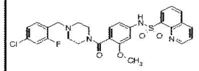 | B | A | B | B | | | | | | | | |
| 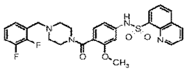 | B | B | B | B | | | | | | | | |
| 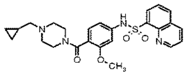 | B | A | B | B | | | | | | | | |
| 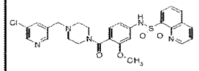 | B | A | A | A | | | | | | | | |
| 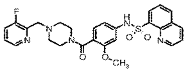 | A | B | B | B | | | | | | | | |
| 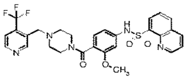 | B | A | B | B | | | | | | | | |

FIG. 1FF
| | | | | | | | | | | | | |
|---|---|---|---|---|---|---|---|---|---|---|---|---|
| 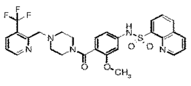 | B | B | B | B | | | | | | | | |
| 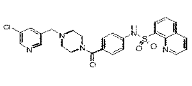 | B | B | A | B | | | | | | | | |
| 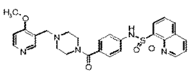 | B | B | B | B | | | | | | | | |
| 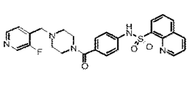 | B | B | B | B | | | | | | | | |
| 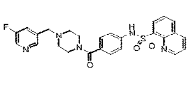 | B | B | B | B | | | | | | | | |
| 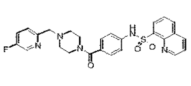 | B | A | A | B | | | | | | | | |
| 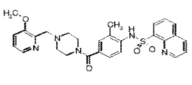 | A | A | B | B | | | | | | | | |
| 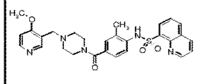 | B | A | B | B | | | | | | | | |
| 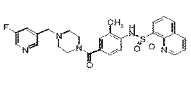 | B | A | B | B | | | | | | | | |
| 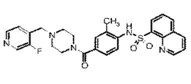 | B | B | B | B | | | | | | | | |
| 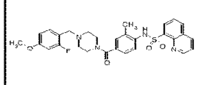 | B | B | B | A | | | | | | | | |
| 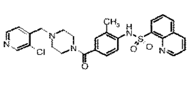 | B | B | A | B | | | | | | | | |
| 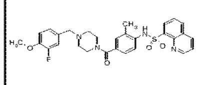 | B | A | B | B | | | | | | | | |
| 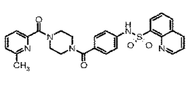 | B | A | A | A | | | | | | | | |
| 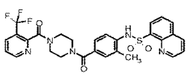 | B | A | B | A | | | | | | | | |

FIG. 1GG
| | | | | | | | | | | | |
|---|---|---|---|---|---|---|---|---|---|---|---|
| 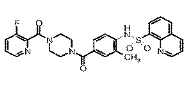 | B | A | A | B | | | | | | | |
| 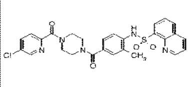 | A | A | B | B | | | | | | | |
| 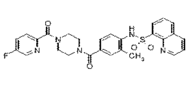 | B | A | B | A | | | | | | | |
| 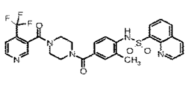 | A | A | B | A | | | | | | | |
| 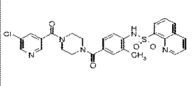 | B | B | A | B | | | | | | | |
| 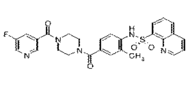 | B | B | B | B | | | | | | | |
| 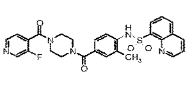 | A | A | B | B | | | | | | | |
| 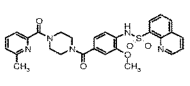 | B | B | B | B | | | | | | | |
| 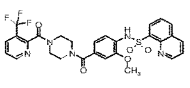 | A | A | A | A | | | | | | | |
| 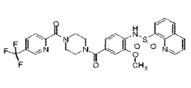 | B | B | B | A | | | | | | | |
| 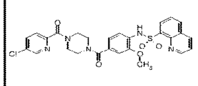 | A | A | B | B | | | | | | | |
| 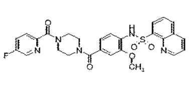 | B | A | B | B | | | | | | | |
| 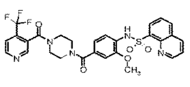 | B | B | B | B | | | | | | | |
| 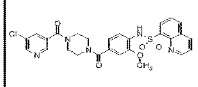 | B | B | B | B | | | | | | | |
| 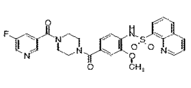 | B | A | B | B | | | | | | | |

FIG. 1 HH
| | | | | | | | | | | | | |
|---|---|---|---|---|---|---|---|---|---|---|---|---|
| 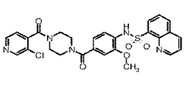 | B | A | A | B | | | | | | | | |
| 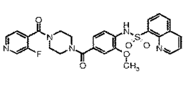 | B | B | B | B | | | | | | | | |
| 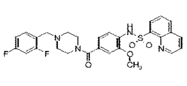 | B | B | B | B | | | | | | | | |
| 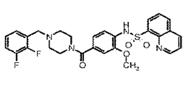 | B | B | B | B | | | | | | | | |
| 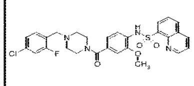 | B | B | B | B | | | | | | | | |
| 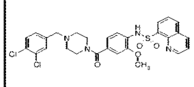 | B | B | B | B | | | | | | | | |
| 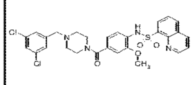 | B | A | A | A | | | | | | | | |
| 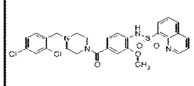 | B | A | A | A | | | | | | | | |
| 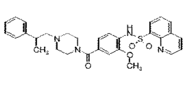 | B | A | B | B | | | | | | | | |
| 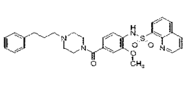 | B | B | A | A | | | | | | | | |
| 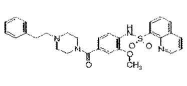 | B | B | B | B | | | | | | | | |
| 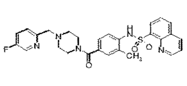 | B | B | B | B | | | | | | | | |
| 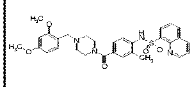 | B | B | B | B | | | | | | | | |
| 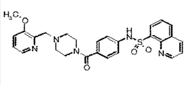 | B | B | B | B | AA | BB | AA | AA | | BB | | AA |
| 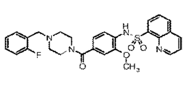 | A | A | B | B | | | | | | | | |

FIG. 1II
| | | | | | | | | | | | |
|---|---|---|---|---|---|---|---|---|---|---|---|
| 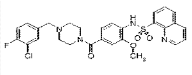 | A | B | B | B | | | | | | | |
| 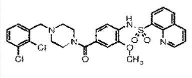 | A | B | B | B | | | | | | | |
| 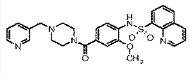 | B | B | B | B | | | | | | | |
| 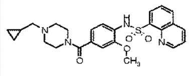 | B | A | B | B | | | | | | | |
| 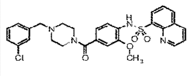 | A | B | A | B | | | | | | | |
| 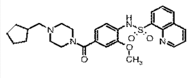 | B | B | B | B | | | | | | | |
| 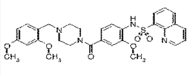 | A | A | A | B | | | | | | | |
| 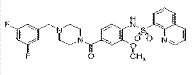 | B | A | B | B | | | | | | | |
| 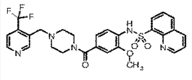 | A | A | B | B | | | | | | | |
| 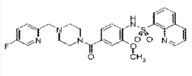 | A | B | B | B | | | | | | | |
| 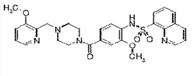 | B | A | B | B | | | | | | | |
| 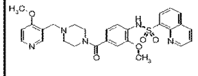 | B | A | B | B | | | | | | | |
| 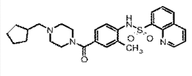 | B | B | B | B | AA | AA | AA | AA | | | |
| 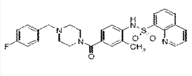 | B | B | B | B | | | | | | | |
| 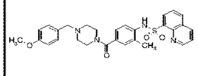 | B | B | B | B | | | | | | | |

FIG. 1JJ
| | | | | | | | | | | | | |
|---|---|---|---|---|---|---|---|---|---|---|---|---|
| 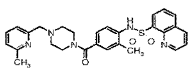 | B | B | B | B | | | | | | | | |
| 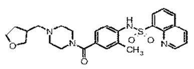 | B | B | B | B | | | | | | | | |
| 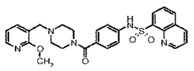 | B | B | B | B | AA | BB | AA | AA | | | | |
| 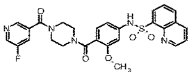 | B | B | B | B | | | | | | | | |
| 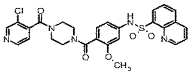 | B | B | B | B | | | | | | | | |
| 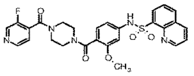 | B | B | B | B | | | | | | | | |
| 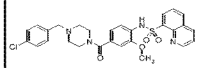 | A | B | B | B | | | | | | | | |
| 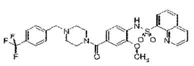 | B | B | B | B | | | | | | | | |
| 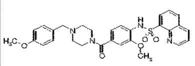 | B | B | B | B | | | | | | | | |
| 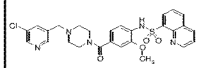 | B | B | B | B | | | | | | | | |
| 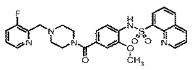 | A | A | B | A | | | | | | | | |
| 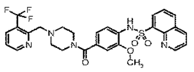 | B | A | B | B | | | | | | | | |
| 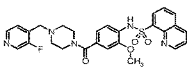 | A | B | B | B | | | | | | | | |
| 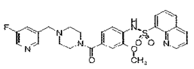 | B | B | B | B | | | | | | | | |
| 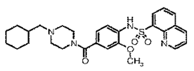 | A | A | B | B | | | | | | | | |

FIG. 1KK
| | | | | | | | | | | | |
|---|---|---|---|---|---|---|---|---|---|---|---|
| 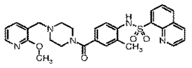 | A | B | B | B | | | | | | | |
| 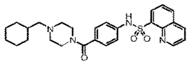 | A | B | B | B | | | | | | | |
| 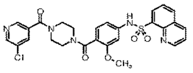 | B | B | B | B | AA | BB | AA | | | | |
| 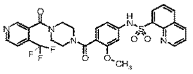 | B | B | B | B | BB | CC | BB | | | | |
| 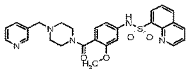 | B | B | B | B | | | | | | | |
| 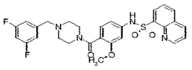 | B | B | B | B | | | | | | | |
| 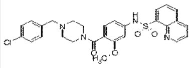 | B | A | A | A | | | | | | | |
| 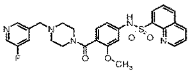 | B | B | B | B | | | | | | | |
| 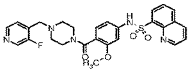 | B | B | B | B | | | | | | | |
| 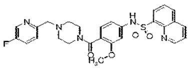 | B | B | B | B | | | | | | | |
| 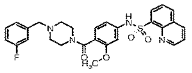 | B | B | B | B | | | | | | | |
| 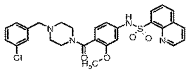 | A | A | B | B | | | | | | | |
| 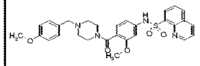 | A | A | B | B | | | | | | | |
| 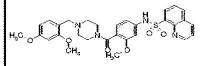 | B | A | B | B | | | | | | | |
| 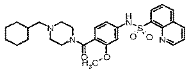 | B | B | B | B | | | | | | | |

FIG. 1LL
| | | | | | | | | | | | |
|---|---|---|---|---|---|---|---|---|---|---|---|
| 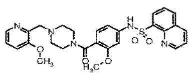 | A | A | B | B | | | | | | | |
| 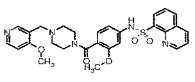 | A | A | B | B | | | | | | | |
| 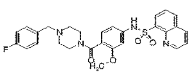 | A | A | B | B | | | | | | | |
| 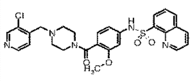 | B | A | B | B | | | | | | | |
| 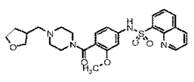 | B | B | B | B | | | | | | | |
| 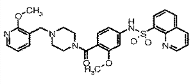 | B | B | B | B | | | | | | | |
| 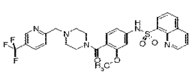 | B | B | B | B | | | | | | | |
| 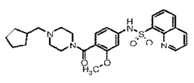 | B | B | B | B | | | | | | | |
| 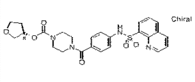 | B | B | B | B | | | | | | | |
| 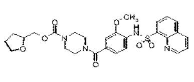 | B | B | B | B | | | | | | | |
| 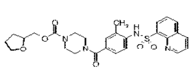 | B | B | B | B | | | | | | | |
| 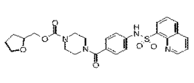 | B | B | B | B | CC | | CC | CC | | | |
| 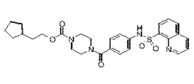 | B | B | B | B | | | | | | | |
| 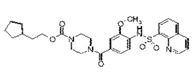 | B | B | B | B | AA | BB | AA | | | | |
| 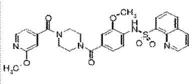 | B | B | B | B | | | | | | | |

FIG. 1MM
| | | | | | | | | | | | |
|---|---|---|---|---|---|---|---|---|---|---|---|
| 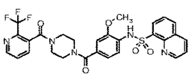 | B | B | B | B | | | | | | | |
| 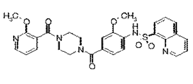 | B | B | B | B | | | | | | | |
| 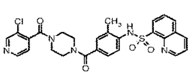 | B | B | B | B | | | | | | | |
| 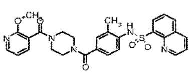 | B | B | B | B | | AA | | | | BB | | |
| 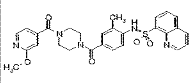 | B | B | B | B | | | | | | | |
| 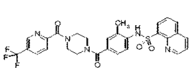 | B | B | B | B | | | | | | | |
| 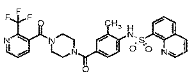 | B | B | B | B | | | | | | | |
| 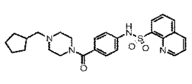 | B | B | B | B | AA | AA | AA | AA | | | | |
| 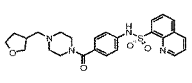 | B | B | B | B | AA | CC | AA | BB | BB | BB | CC | AA |
| 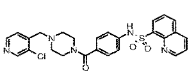 | B | B | B | B | | | | | | | |
| 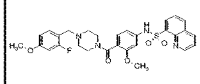 | B | B | A | A | | | | | | | |
| 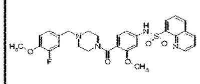 | B | B | B | B | | | | | | | |
| 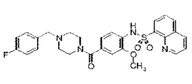 | A | A | B | A | | | | | | | |
| 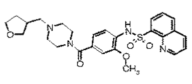 | A | A | A | B | | | | | | | |
| 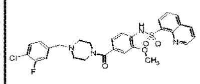 | B | A | B | A | | | | | | | |

FIG. 1NN
| | | | | | | | | | | | |
|---|---|---|---|---|---|---|---|---|---|---|---|
| 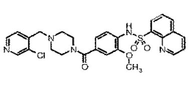 | A | A | B | A | | | | | | | |
| 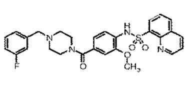 | A | A | A | B | | | | | | | |
| 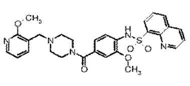 | A | B | A | B | | | | | | | |
| 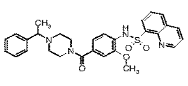 | A | B | A | B | | | | | | | |
| 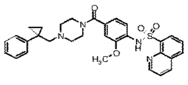 | A | A | A | B | | | | | | | |
| 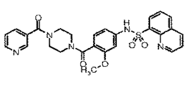 | A | A | B | A | | | | | | | |
| 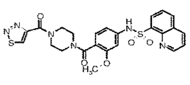 | B | A | B | B | | | | | | | |
| 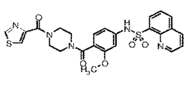 | A | A | A | A | | | | | | | |
| 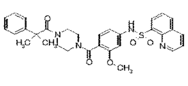 | B | B | B | B | | | | | | | |
| 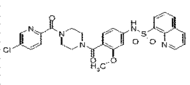 | B | B | B | B | | | | | | | |
| 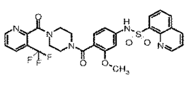 | B | B | B | B | | | | | | | |
| 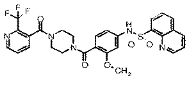 | B | B | B | B | | | | | | | |
| 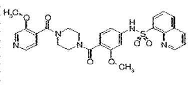 | B | B | B | B | | | | | | | |
| 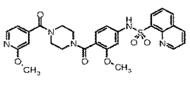 | B | B | B | B | | | | | | | |
| 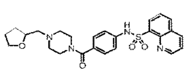 | B | B | B | B | | | | | | | |

FIG. 100
| | | | | | | | | | | | | |
|---|---|---|---|---|---|---|---|---|---|---|---|---|
| 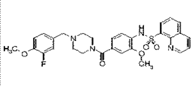 | B | B | B | B | | | | | | | | |
| 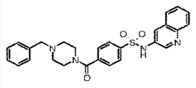 | B | B | B | B | | | | | | | | |
| 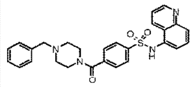 | B | B | B | B | | | | | | | | |
| 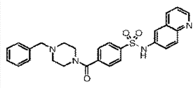 | B | B | A | B | | | | | | | | |
| 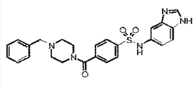 | B | B | A | B | | | | | | | | |
| 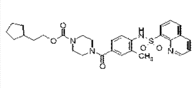 | A | B | A | B | | | | | | | | |
| 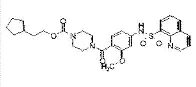 | A | B | B | B | | | | | | | | |
| 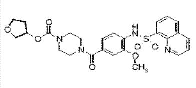 | B | B | B | B | | | | | | | | |
| 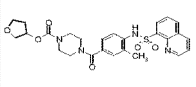 | B | B | B | B | | | | | | | | |
| 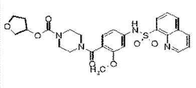 | B | B | B | B | | | | | | | | |
| 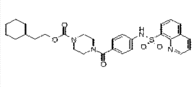 | A | B | A | B | | | | | | | | |
| 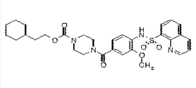 | A | B | A | B | | | | | | | | |
| 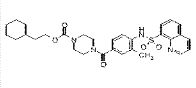 | A | A | A | A | | | | | | | | |
| 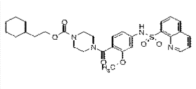 | B | B | B | B | | | | | | | | |
| 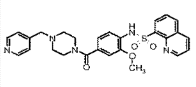 | B | A | B | A | | | | | | | | |

FIG. 1PP
| | | | | | | | | | | | | |
|---|---|---|---|---|---|---|---|---|---|---|---|---|
| 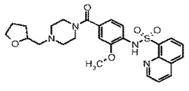 | B | B | A | B | | | | | | | | |
| 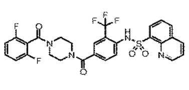 | B | B | A | B | | | | | | | | |
| 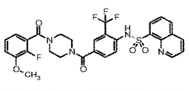 | A | B | A | A | | | | | | | | |
| 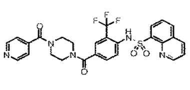 | B | B | A | B | | | | | | | | |
| 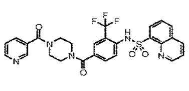 | B | B | B | B | | | | | | | | |
| 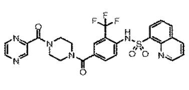 | B | B | B | B | | | | | | | | |
| 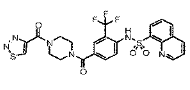 | B | B | B | B | | | | | | | | |
| 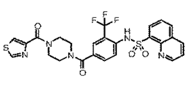 | B | B | B | B | | | | | | | | |
| 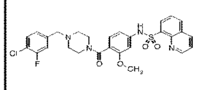 | B | B | B | B | | | | | | | | |
| 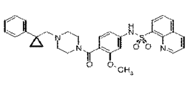 | B | B | B | B | | | | | | | | |
| 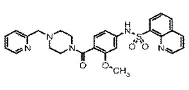 | B | B | A | B | | | | | | | | |
| 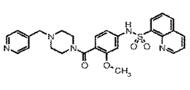 | B | B | B | B | | | | | | | | |
| 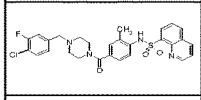 | B | B | B | B | | | | | | | | |
| 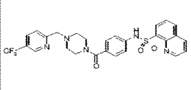 | B | B | B | B | CC | CC | BB | CC | | | | |
| 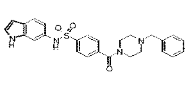 | B | A | B | B | | | | | | | | |

FIG. 1QQ
| | | | | | | | | | | | | |
|---|---|---|---|---|---|---|---|---|---|---|---|---|
| 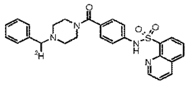 | B | B | B | B | AA | AA | AA | AA | | | | |
| 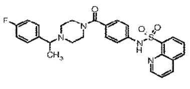 | B | B | B | A | | | | | | | | |
| 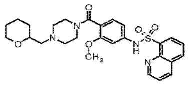 | B | B | A | B | | | | | | | | |
| 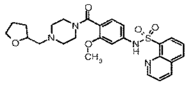 | B | B | A | B | | | | | | | | |
| 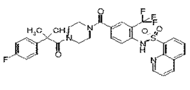 | A | B | B | B | | | | | | | | |
| 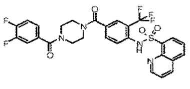 | B | A | B | B | | | | | | | | |
| 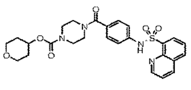 | B | A | B | B | | | | | | | | |
| 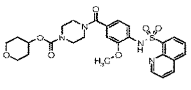 | B | B | B | B | | | | | | | | |
| 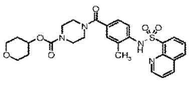 | B | B | B | B | | | | | | | | |
| 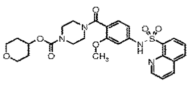 | B | B | A | A | | | | | | | | |
| 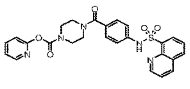 | B | B | B | B | | | | | | | | |
| Chiral 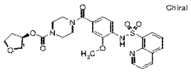 | B | A | B | B | | | | | | | | |
| Chiral 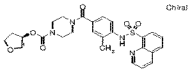 | B | B | B | B | | | | | | | | |
| 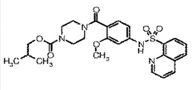 | B | B | B | B | | | | | | | | |
| Chiral 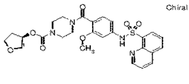 | B | B | B | B | CC | | CC | | | | | |

FIG. 1RR
| | | | | | | | | | | | | |
|---|---|---|---|---|---|---|---|---|---|---|---|---|
| 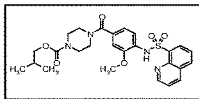 | B | B | B | B | | | | | | | | |
| 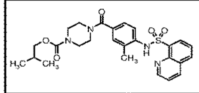 | B | B | B | B | | | | | | | | |
| 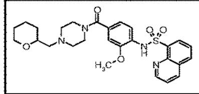 | B | B | B | B | | | | | | | | |
| 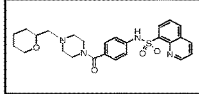 | B | B | B | B | BB | CC | BB | BB | | | | |
| 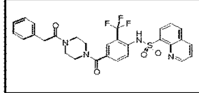 | B | B | B | B | | | | | | | | |
| 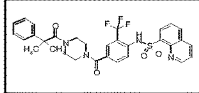 | B | B | B | B | | | | | | | | |
| 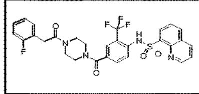 | B | B | B | B | | | | | | | | |
| 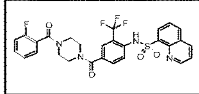 | B | B | B | B | | | | | | | | |
| 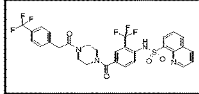 | B | B | B | B | | | | | | | | |
| 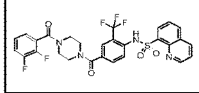 | B | B | B | B | | | | | | | | |
| 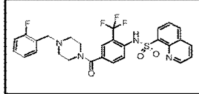 | B | A | A | A | | | | | | | | |
| 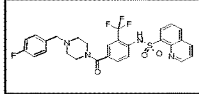 | A | A | B | A | | | | | | | | |
| 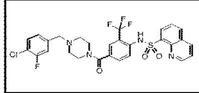 | A | A | B | B | | | | | | | | |
| 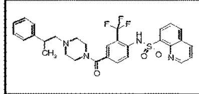 | B | B | B | B | | | | | | | | |
| 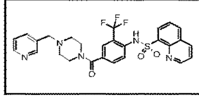 | B | B | B | B | | | | | | | | |

FIG. 1SS
| | | | | | | | | | | | | |
|---|---|---|---|---|---|---|---|---|---|---|---|---|
| 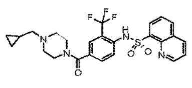 | A | A | B | B | | | | | | | | |
| 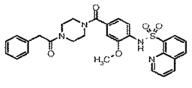 | B | B | B | B | | | | | | | | |
| 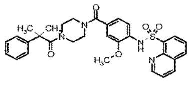 | B | B | B | B | | | | | | | | |
| 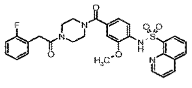 | B | B | B | B | | | | | | | | |
| 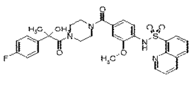 | B | B | B | B | | | | | | | | |
| 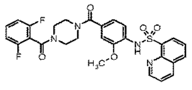 | A | B | B | B | | | | | | | | |
| 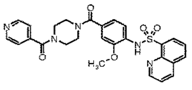 | A | A | B | B | | | | | | | | |
| 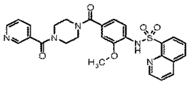 | B | B | B | B | | | | | | | | |
| 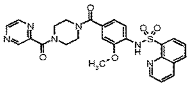 | A | A | B | B | | | | | | | | |
| 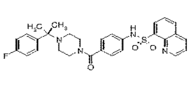 | B | B | B | A | | | | | | | | |
| 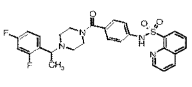 | B | B | B | B | | | | | | | | |
| 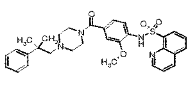 | B | B | B | B | | | | | | | | |
| 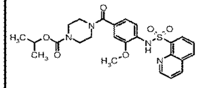 | A | B | B | A | | | | | | | | |
| 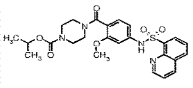 | A | B | B | B | | | | | | | | |
| 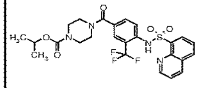 | B | A | B | B | | | | | | | | |

FIG. 1TT
| | | | | | | | | | | | | |
|---|---|---|---|---|---|---|---|---|---|---|---|---|
| 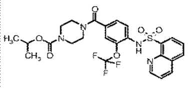 | B | B | B | B | | | | | | | | |
| 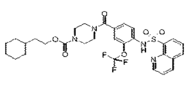 | B | A | B | B | | | | | | | | |
| 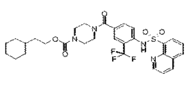 | B | A | B | A | | | | | | | | |
| 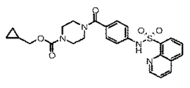 | B | B | B | B | | | | | | | | |
| 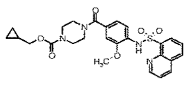 | B | A | B | A | | | | | | | | |
| 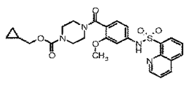 | B | A | B | B | | | | | | | | |
| 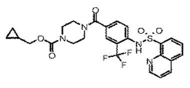 | B | A | B | B | | | | | | | | |
| 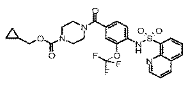 | B | B | B | B | | | | | | | | |
| 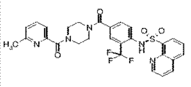 | B | B | B | B | | | | | | | | |
| 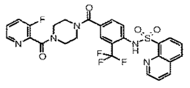 | B | B | B | B | | | | | | | | |
| 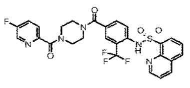 | B | B | B | B | | | | | | | | |
| 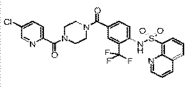 | B | B | A | A | | | | | | | | |
| 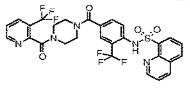 | B | B | B | B | | | | | | | | |
| 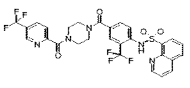 | B | B | B | B | | | | | | | | |
| 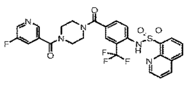 | B | B | B | B | | | | | | | | |

FIG. 1UU
| | | | | | | | | | | | | |
|---|---|---|---|---|---|---|---|---|---|---|---|---|
| 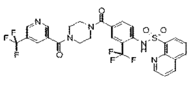 | B | B | B | B | | | | | | | | |
| 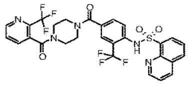 | B | B | B | B | | | | | | | | |
| 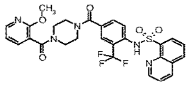 | B | B | B | B | | | | | | | | |
| 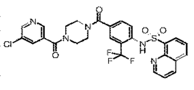 | B | B | B | B | | | | | | | | |
| 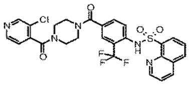 | B | B | B | B | | | | | | | | |
| 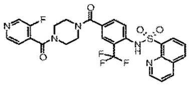 | B | B | B | B | | | | | | | | |
| 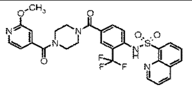 | A | B | A | B | | | | | | | | |
| 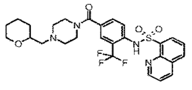 | A | A | A | A | | | | | | | | |
| 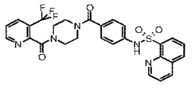 | B | A | A | B | | | | | | | | |
| 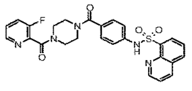 | B | B | B | B | | | | | | | | |
| 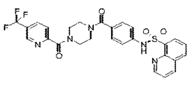 | B | A | B | B | | | | | | | | |
| 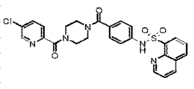 | B | A | A | B | | | | | | | | |
| 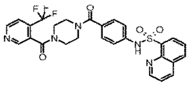 | B | A | A | A | | | | | | | | |
| 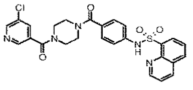 | A | B | B | B | | | | | | | | |
| 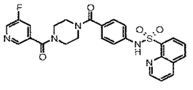 | B | B | B | B | | | | | | | | |

FIG. 1 VV
| | | | | | | | | | | | |
|---|---|---|---|---|---|---|---|---|---|---|---|
| 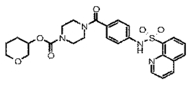 | A | A | B | A | | | | | | | |
| 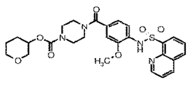 | B | B | B | B | | | | | | | |
| 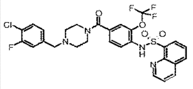 | A | B | A | A | | | | | | | |
| 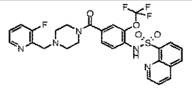 | B | B | B | B | | | | | | | |
| 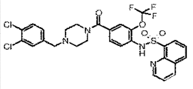 | B | B | B | B | | | | | | | |
| 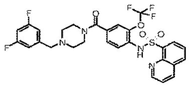 | B | A | B | B | | | | | | | |
| 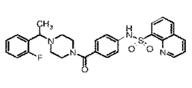 | B | B | B | B | | | | | | | |
| 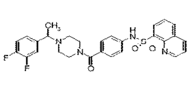 | B | B | B | B | AA | AA | | | | | |
| 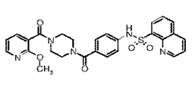 | B | B | B | B | | | | | | | |
| 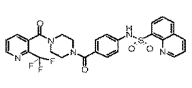 | B | B | B | B | | | | | | | |
| 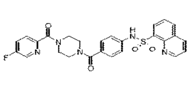 | B | A | A | B | | | | | | | |
| 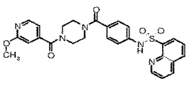 | B | A | A | A | | | | | | | |
| 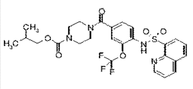 | A | A | B | B | | | | | | | |
| 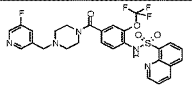 | A | A | B | A | | | | | | | |
| 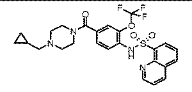 | B | B | B | B | | | | | | | |

FIG. 1 WW
| | | | | | | | | | | | |
|---|---|---|---|---|---|---|---|---|---|---|---|
| 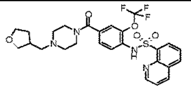 | A | B | A | A | | | | | | | |
| 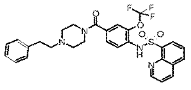 | B | A | B | A | | | | | | | |
| 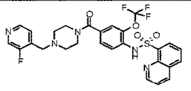 | B | A | A | A | | | | | | | |
| 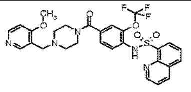 | B | B | B | A | | | | | | | |
| 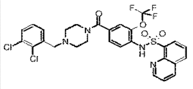 | B | B | B | A | | | | | | | |
| 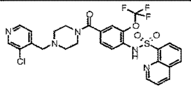 | A | A | A | A | | | | | | | |
| 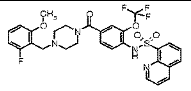 | B | B | B | B | | | | | | | |
| 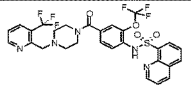 | A | B | B | B | | | | | | | |
| 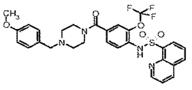 | B | B | A | B | | | | | | | |
| 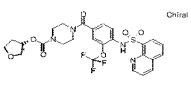 | B | A | B | B | | | | | | | |
| 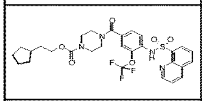 | A | A | A | A | | | | | | | |
| 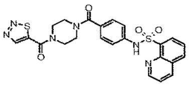 | B | B | B | B | AA | CC | AA | | | | |
| 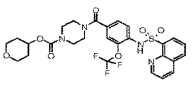 | B | B | B | B | | | | | | | |
| 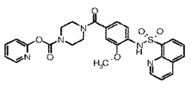 | B | B | B | B | | | | | | | |
| 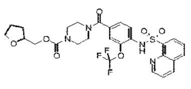 | B | B | B | B | | | | | | | |

FIG. 1XX
| | | | | | | | | | | | |
|---|---|---|---|---|---|---|---|---|---|---|---|
| 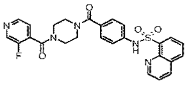 | B | B | B | B | | | | | | | |
| 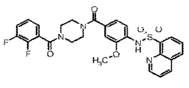 | B | B | B | B | | | | | | | |
| 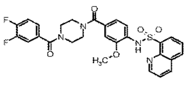 | B | B | B | B | | | | | | | |
| 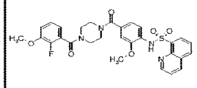 | B | B | B | B | | | | | | | |
| 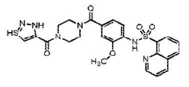 | B | B | B | B | | CC | | | | | |
| 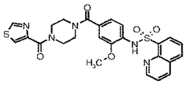 | A | B | A | A | | | | | | | |
| 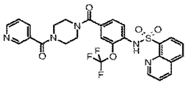 | A | B | B | A | | | | | | | |
| 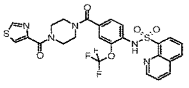 | A | B | B | B | | | | | | | |
| 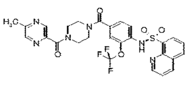 | B | B | B | B | | | | | | | |
| 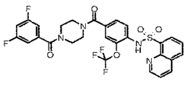 | B | B | B | B | | | | | | | |
| 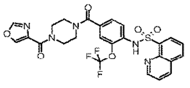 | B | B | B | B | | | | | | | |
| 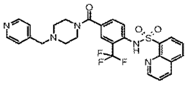 | B | B | A | A | | | | | | | |
| 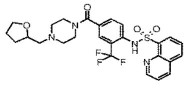 | B | A | A | A | | | | | | | |
| 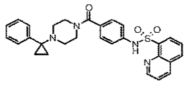 | B | B | B | B | | | | | | | |
| 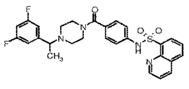 | B | B | A | B | | | | | | | |

FIG. 1YY
| | | | | | | | | | | | |
|---|---|---|---|---|---|---|---|---|---|---|---|
| 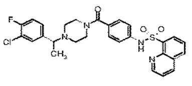 | B | B | A | B | | | | | | | |
| 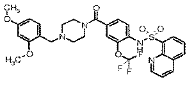 | B | B | A | B | | | | | | | |
| 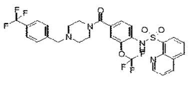 | B | B | A | B | | | | | | | |
| 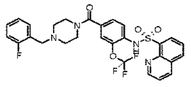 | B | B | B | B | | | | | | | |
| 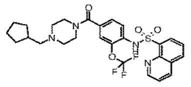 | A | A | B | A | | | | | | | |
| 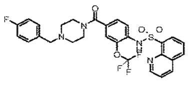 | A | A | A | B | | | | | | | |
| 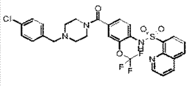 | B | A | A | B | | | | | | | |
| 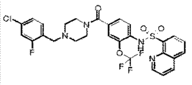 | B | B | B | B | | | | | | | |
| 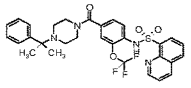 | B | B | B | B | | | | | | | |
| 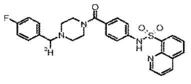 | B | A | A | B | | | | | | | |
| 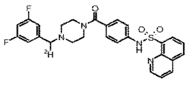 | B | A | B | B | | | | | | | |
| 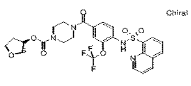 | A | A | B | B | | | | | | | |
| 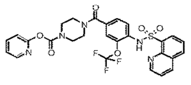 | B | A | A | B | | | | | | | |
| 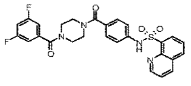 | B | B | B | B | | | | | | | |
| 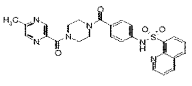 | A | A | A | B | | | | | | | |

FIG. 1ZZ
| | | | | | | | | | | | | |
|---|---|---|---|---|---|---|---|---|---|---|---|---|
| 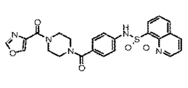 | B | B | B | B | | | | | | | | |
| 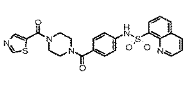 | B | B | B | A | | | | | | | | |
| 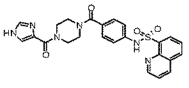 | B | A | B | B | | | | | | | | |
| 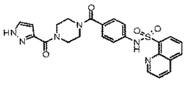 | B | B | B | B | | | | | | | | |
| 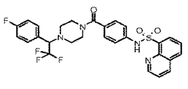 | A | B | A | B | | | | | | | | |
| 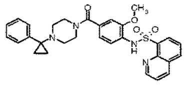 | B | B | A | B | | | | | | | | |
| 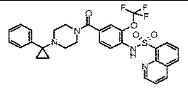 | B | B | A | A | | | | | | | | |
| 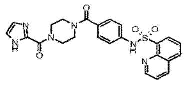 | B | A | B | B | | | | | | | | |
| 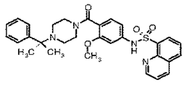 | B | B | B | B | | | | | | | | |
| 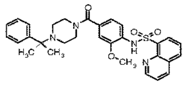 | B | B | B | B | | | | | | | | |
| 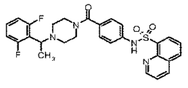 | B | B | B | B | | | | | | | | |
| 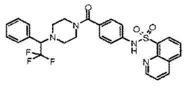 | B | B | B | B | | | | | | | | |
| 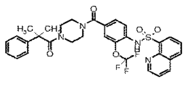 | B | A | A | B | | | | | | | | |
| 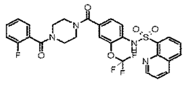 | B | B | B | B | | | | | | | | |
| 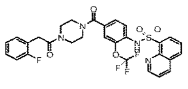 | B | B | B | B | | | | | | | | |

FIG. 1 AAA
| | | | | | | | | | | | |
|---|---|---|---|---|---|---|---|---|---|---|---|
| 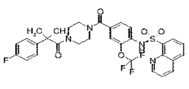 | B | B | B | B | | | | | | | |
| 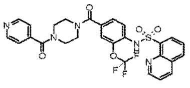 | B | B | B | B | | | | | | | |
| 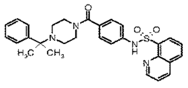 | B | B | B | B | | | | | | | |
| 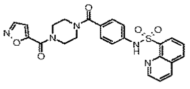 | B | B | B | B | BB | CC | | | | | |
| 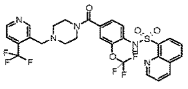 | B | B | B | B | | | | | | | |
| 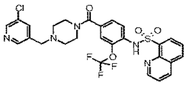 | B | B | B | B | | | | | | | |
| 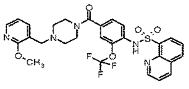 | A | A | A | A | | | | | | | |
| 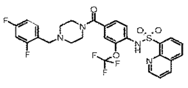 | A | A | B | B | | | | | | | |
| 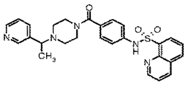 | A | A | B | B | | | | | | | |
| 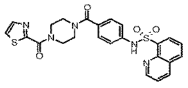 | B | B | B | B | | | | | | | |
| 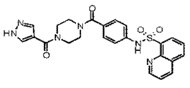 | B | B | B | B | | | | | | | |
| 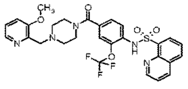 | B | A | A | B | | | | | | | |
| 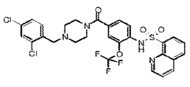 | B | B | B | B | | | | | | | |
| 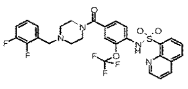 | B | B | B | B | | | | | | | |
| 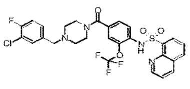 | B | B | B | B | | | | | | | |

FIG. 1 BBB
| | | | | | | | | | | | | |
|---|---|---|---|---|---|---|---|---|---|---|---|---|
| 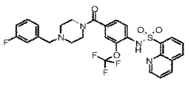 | B | B | B | B | | | | | | | | |
| 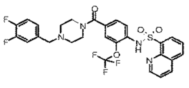 | B | B | B | B | | | | | | | | |
| 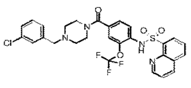 | A | A | A | A | | | | | | | | |
| 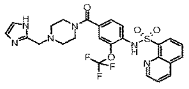 | B | B | B | B | | | | | | | | |
| 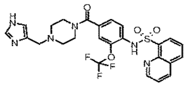 | B | A | B | B | | | | | | | | |
| 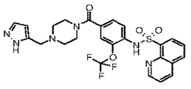 | B | B | A | A | | | | | | | | |
| 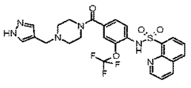 | B | B | A | A | | | | | | | | |
| 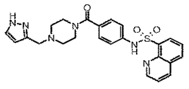 | B | B | A | B | AA | CC | AA | BB | | | | |
| 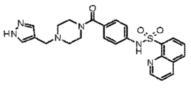 | B | B | B | B | AA | AA | AA | AA | | AA | | AA |
| 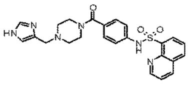 | B | B | B | B | | | | | | | | |
| 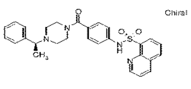 | B | B | B | B | | | | | | | | |
| 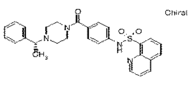 | B | B | B | B | AA | AA | AA | AA | | | | |
| 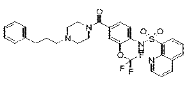 | B | B | B | B | | | | | | | | |
| 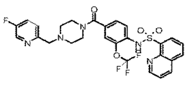 | B | B | B | B | | | | | | | | |
| 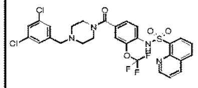 | B | B | B | B | | | | | | | | |

FIG. 1 CCC
| | | | | | | | | | | | |
|---|---|---|---|---|---|---|---|---|---|---|---|
| 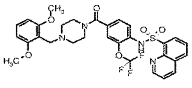 | B | B | B | B | | | | | | | |
| 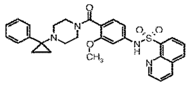 | A | B | B | B | | | | | | | |
| 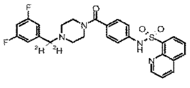 | B | B | B | B | | | | | | | |
| 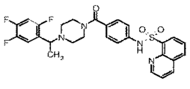 | A | B | A | A | | | | | | | |
| 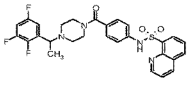 | B | A | A | A | | | | | | | |
| 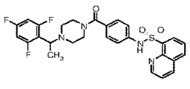 | B | B | B | B | | | | | | | |
| 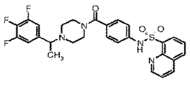 | A | A | A | A | | | | | | | |
| 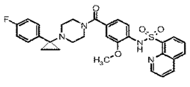 | A | A | A | A | | | | | | | |
| 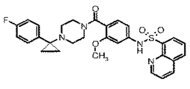 | A | A | A | A | | | | | | | |
| 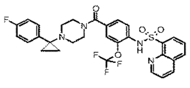 | A | A | A | B | | | | | | | |
| 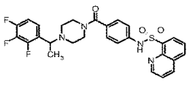 | A | A | A | A | | | | | | | |
| 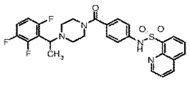 | A | A | A | A | | | | | | | |
| 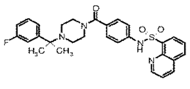 | A | A | A | A | | | | | | | |
| 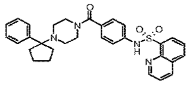 | A | A | A | A | | | | | | | |
| 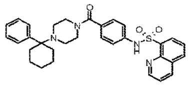 | B | B | B | B | | | | | | | |

FIG. 1 DDD
| | | | | | | | | | | | | |
|---|---|---|---|---|---|---|---|---|---|---|---|---|
| 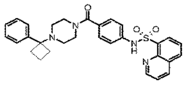 | A | B | B | B | | AA | | | | | | |
| 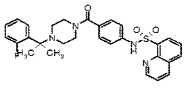 | B | B | B | A | | | | | | | | |
| 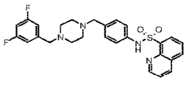 | B | B | B | B | | | | | | | | |
| 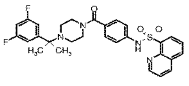 | A | A | B | B | | | | | | | | |
| 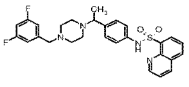 | A | A | A | A | | | | | | | | |
| 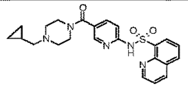 | B | A | A | B | CC | CC | CC | | | | | |
| 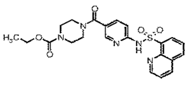 | A | A | A | A | | | | | | | | |
| 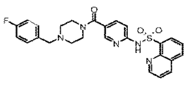 | B | A | A | A | | | | | | | | |
| 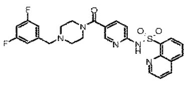 | B | A | A | A | CC | CC | BB | | | | | |
| 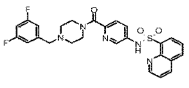 | B | B | B | B | | | | | | | | |
| 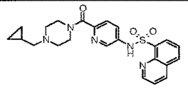 | A | B | A | A | CC | CC | CC | | | | | |
| 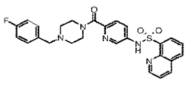 | B | A | A | A | | | | | | | | |
| 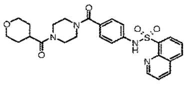 | B | B | A | B | | | | | | | | |
| 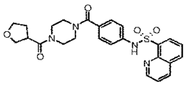 | B | B | B | B | | | | | | | | |
| 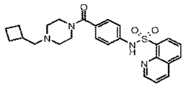 | B | A | A | A | AA | AA | AA | AA | | | | |

FIG. 1EEE
| | | | | | | | | | | | | |
|---|---|---|---|---|---|---|---|---|---|---|---|---|
| 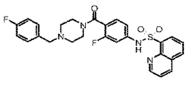 | A | A | B | B | | | | | | | | |
| 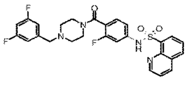 | B | A | B | B | | | | | | | | |
| 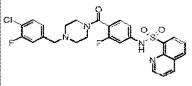 | A | A | B | A | | | | | | | | |
| 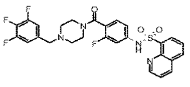 | B | A | B | B | | | | | | | | |
| 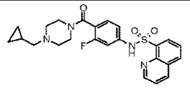 | A | A | B | B | | | | | | | | |
| 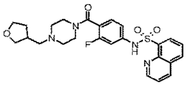 | B | A | B | B | BB | CC | BB | BB | BB | BB | CC | BB |
| 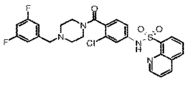 | B | A | B | B | | | | | | | | |
| 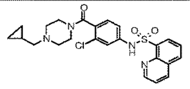 | B | A | B | B | | | | | | | | |
| 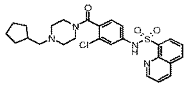 | A | A | B | B | | | | | | | | |
| 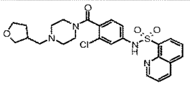 | B | B | B | B | BB | CC | BB | | | | | |
| 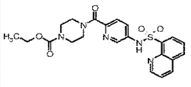 | A | B | B | A | | | | | | | | |
| 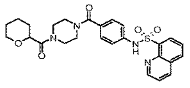 | B | A | B | B | | | | | | | | |
| 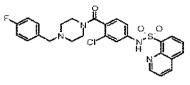 | B | B | B | A | | | | | | | | |
| 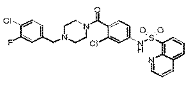 | B | B | B | B | | | | | | | | |
| 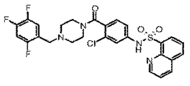 | B | B | B | B | | | | | | | | |

FIG. 1FFF
| | | | | | | | | | | | | |
|---|---|---|---|---|---|---|---|---|---|---|---|---|
| 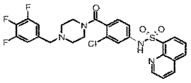 | B | B | B | B | | | | | | | | |
| 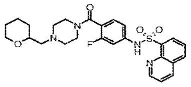 | B | B | B | B | BB | CC | BB | BB | | | | |
| 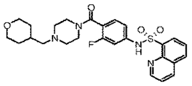 | A | B | B | B | AA | BB | AA | BB | AA | CC | | AA |
| 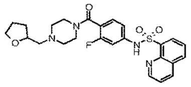 | B | B | B | B | | CC | BB | BB | BB | CC | CC | BB |
| 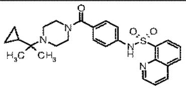 | A | A | B | B | AA | AA | AA | AA | | AA | | AA |
| 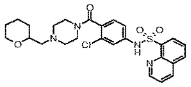 | A | A | A | A | | | | | | | | |
| 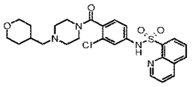 | A | A | A | A | | | | | | | | |
| 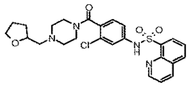 | A | A | A | A | | | | | | | | |
| 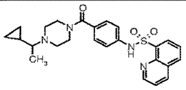 | A | A | A | A | AA | BB | AA | AA | | | | |
| 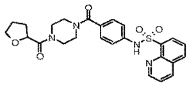 | A | A | B | B | | | | | | | | |

PYRUVATE KINASE ACTIVATORS FOR USE IN THERAPY

This application is a continuation of U.S. Ser. No. 14/115,289, filed Feb. 11, 2014, and published as U.S. Pat. No. 9,193,701, which is a national stage application under 35 U.S.C. §371 of International Application No. PCT/US2012/036412, filed May 3, 2012, and published as International Publication No. WO 2012/151451 on Nov. 8, 2012, which claims priority from U.S. Ser. No. 61/482,171, filed May 3, 2011, the contents of each of which is incorporated herein by reference in its entirety.

Pyruvate kinase deficiency (PKD) is one of the most common enzyme defects in erythrocytes in human due to autosomal recessive mutations of the PKLR gene (Zanella, A., et al., *Br J Haematol* 2005, 130 (1), 11-25). It is also the most frequent enzyme mutation in the central glycolytic pathway and only second to glucose-6 phosphate dehydrogenase (G6PD) deficiency (Kedar, P., et al., *Clin Genet* 2009, 75 (2), 157-62) of the hexose monophosphate shunt.

Human erythrocytes are unique in that they anucleate when mature Immature erythocytes have nuclei but during early erythropoiesis prior to becoming circulating reticulocytes they extrude nuclei as well as other organelles such as mitochondria, endoplasmic reticulum, and golgi aparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate NAD through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic hemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}$>Met associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet* 2009, 75 (2), 157-62; Fermo, E. et al., *Br J Haematol* 2005, 129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}$>Trp and $Arg^{510}$>Gln, while mutations $Arg^{479}$>His, $Arg^{490}$>Trp and $Asp^{331}$>Gly were more frequently found in Asian patients (Kedar, P., et al., *Clin Genet* 2009, 75 (2), 157-62).

The present invention provides a method for increasing lifetime of the red blood cells (RBCs) in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention further provides a method for regulating 2,3-diphosphoglycerate levels in blood in need thereof comprising contacting blood with an effective amount of (1) a compound disclosed herein or a pharmaceutically acceptable salt thereof; (2) a composition comprising a compound disclosed herein or a salt thereof and a carrier; or (3) a pharmaceutical composition comprising a compound disclosed herein or a pharmaceutically acceptable salt thereof, and a pharmaceutically acceptable carrier.

The present invention also provides a method for treating hereditary non-spherocytic hemolytic anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating sickle cell anemia comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

The present invention further provides a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt thereof; (2) a pharmaceutical composition comprising a compound disclosed herein or a pharmaceutically acceptable salt thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2, 3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

In one embodiment, provided is a pharmaceutical composition comprising a compound or a pharmaceutically acceptable salt of formula (I):

(I)

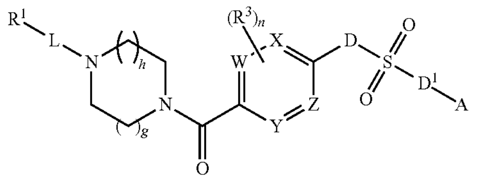

wherein:

W, X, Y and Z are each independently selected from CH or N;

D and $D^1$ are independently selected from a bond or $NR^b$;

A is optionally substituted aryl or optionally substituted heteroaryl;

L is a bond, —C(O)—, $—(CR^cR^c)_m—$, —OC(O)—, $—(CR^cR^c)_m—OC(O)—$, $—(CR^cR^c)_m—C(O)—$, $—NR^bC(S)—$, or $—NR^bC(O)—$ (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl; each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^aR^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2.

BRIEF DESCRIPTION OF THE FIGURES

FIG. 1 represents a table of exemplary compounds.

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that activate wild type PKR and/or various mutant PKRs such as those described herein.

In one embodiment, provided is a compound of formula (I) or a pharmaceutically acceptable salt thereof, or a pharmaceutical composition comprising a compound of formula (I) or a pharmaceutically acceptable salt thereof:

(I)

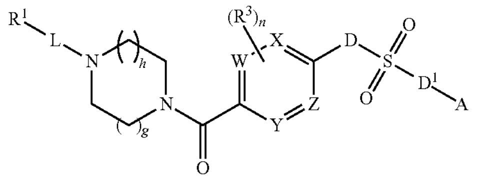

wherein:

W, X, Y and Z are each independently selected from CH or N;

D and $D^1$ are independently selected from a bond or $NR^b$;

A is optionally substituted aryl or optionally substituted heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^b$C(S)—, or —$NR^b$C(O)— (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^aR^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2.

In certain embodiments, provided is a compound of formula (I) or a pharmaceutically acceptable salt thereof:

(I)

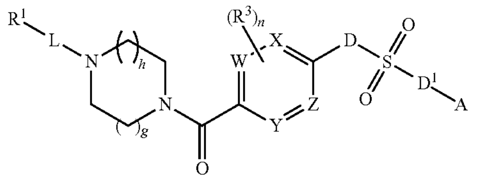

wherein:

W, X, Y and Z are each independently selected from CH or N;

D and $D^1$ are independently selected from a bond or $NR^b$;

A is optionally substituted bicyclic heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^b$C(S)—, or —$NR^b$C(O)—;

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$ or two adjacent $R^3$ taken together with the carbon atoms to which they are attached form an optionally substituted cyclyl; each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —N$R^aR^b$ and —O$R^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2. In some embodiments, h is 1. In some embodiments, h is 2.

In some embodiments, g is 1. In some embodiments, g is 2.

In some embodiments, both h and g are 1. In some embodiments, h is 1 and g is 2. In some embodiments, g is 1 and h is 2.

In some embodiments, W, X, Y and Z are CH. In some embodiments, at least one of W, X, Y and Z is N. In some embodiments, at least two of W, X, Y and Z are N. In some embodiments, at least three of W, X, Y and Z are N.

In some embodiments, W, X, Y, Z and the carbons to which they are attached form a pyridyl ring. In some embodiments, W, X, Y, Z and the carbon atoms to which they are attached form a pyrimidyl ring. In some embodiments, W, X, Y, Z and the carbon atoms to which they are attached form a pyridazinyl ring.

In some embodiments, W, X and Y are CH and Z is N.

In some embodiments, X, Y and Z are CH and W is N.

In some embodiments, D is $NR^b$ and $D^1$ is a bond. In some embodiments, D is a bond and $D^1$ is $NR^b$. In some embodiments, both D and $D^1$ are $NR^b$. In some embodiments, $R^b$ is alkyl (e.g., methyl or ethyl). In some embodiments, $R^b$ is hydrogen (H).

In some embodiments, A is a 9-10 membered bicyclic heteroaryl (e.g., quinazolinyl, quinoxalinyl, cinnolinyl, isoquinolyl, indolyl, benzoxazolyl, pyrrolopyridyl, pyrrolopyrimidyl, benzimidazolyl, benzthiazolyl, or benzoxazolyl). In some embodiments, A is a N-containing 9-10 membered bicyclic heteroaryl. In some embodiments, A is optionally substituted quinazolinyl (e.g., 8-quinazolinyl or 4-quinazolinyl), optionally substituted quinoxalinyl (e.g., 5-quinoxalinyl), optionally substituted quinolinyl (e.g., 4-quinolinyl or 8-quinolinyl), optionally substituted cinnolinyl (e.g., 8-cinnolinyl), optionally substituted isoquinolinyl, optionally substituted indolyl (7-indolyl), optionally substituted benzoxazolyl (e.g., 7-benzoxazolyl), optionally substituted pyrrolopyridyl (e.g., 4-pyrrolopyridyl), optionally substituted pyrrolopyrimidyl (e.g., 4-pyrrolopyrimidyl), optionally substituted benzimidazolyl (e.g., 7-benzimidazolyl), optionally substituted benzthiazolyl (e.g., 4-benzthiazolyl, 2-methyl-4-benzthiazolyl or 7-benzthiazolyl), or optionally substituted benzoxazolyl (e.g., 4-benzoxazolyl). In some embodiments, A is optionally substituted with halo. In some embodiments, A is

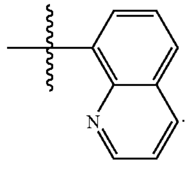 [SMILES: *c1cccc2cccnc12]

In some embodiments, A is

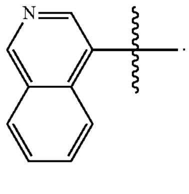 [SMILES: *c1cncc2ccccc12]

In some embodiments, A is optionally substituted

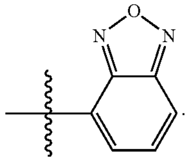 [SMILES: *c1cccc2nonc12]

In some embodiments, A is

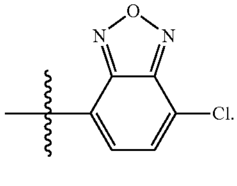 [SMILES: *c1ccc(Cl)c2nonc12]

In some embodiments, L is a bond.

In some embodiments, L is $—(CR^cR^c)_m—$ and m is 1. In some aspects of these embodiments, each $R^c$ is hydrogen. In some aspects of these embodiments, one $R^c$ is alkyl (e.g., methyl or ethyl) and the other $R^c$ is hydrogen. In some aspects of these embodiments, one $R^c$ is halo (e.g., fluoro) and one $R^c$ is hydrogen. In some aspects of these embodiments, both $R^c$ are halo (e.g., fluoro). In some aspects of these embodiments, one $R^c$ is alkoxy (e.g., methoxy or ethoxy) and one $R^c$ is hydrogen. In some aspects of these embodiments, both $R^c$ are alkoxy (e.g., methoxy or ethoxy). In some aspects of these embodiments, two $R^c$ taken together with the carbon to which they are attached form a cycloalkyl (e.g., cyclopropyl).

In some embodiments, L is $—(CR^cR^c)_m—$ and m is 2. In some aspects of these embodiments, each $R^c$ is hydrogen. In some aspects of these embodiments, 1 $R^c$ is alkyl (e.g., methyl or ethyl) and each of the other $R^c$ are hydrogen. In some aspects of these embodiments, two $R^c$s taken together with the carbon to which they are attached form a cycloalkyl (e.g., cyclopropyl) and each of the other two $R^c$s are hydrogen.

In some embodiments, L is $—(CR^cR^c)_m—$ and m is 3. In some aspects of these embodiments each $R^c$ is hydrogen.

In some embodiments, L is —C(O)—.

In some embodiments, L is —O—C(O)—.

In some embodiments, L is $NR^bC(O)—$ and $R^b$ is H. In some embodiments, L is $NR^bC(S)—$ and $R^b$ is H.

In some embodiments, L is $—(CR^cR^c)_m—C(O)—$ and m is 1. In some aspects of these embodiments, each $R^c$ is hydrogen. In some aspects of these embodiments, one $R^c$ is alkyl (e.g., methyl or ethyl) and one $R^c$ is hydrogen. In some aspects of these embodiments, both $R^c$ are alkyl (e.g., methyl or ethyl).

In some embodiments, L is $—(CR^cR^c)_m—C(O)—$ and m is 2. In some aspects of these embodiments, each $R^c$ is hydrogen.

In some embodiments, L is $—(CR^cR^c)_m—C(O)—$ and m is 3. In some aspects of these embodiments, each $R^c$ is hydrogen.

In some embodiments, $R^1$ is alkyl substituted with 0-5 occurrences of $R^d$ (e.g., methyl, ethyl, n-propyl, i-propyl, or n-butyl). In some embodiments, $R^1$ is methyl, ethyl, n-propyl, i-propyl, or n-butyl. In some embodiments, $R^1$ is ethyl or propyl (n-propyl or i-propyl). In some aspects of these embodiments, L is a bond, —$CH_2$—, —C(O)—, or —O(CO)—. In some aspects of these embodiments, L is —O(CO)—.

In some embodiments, $R^1$ is alkyl substituted with 1 occurrence of $R^d$ (e.g., methyl, ethyl, n-propyl, i-propyl, or n-butyl). In some embodiments, $R^1$ is methyl, ethyl, or n-propyl substituted with 1 occurrence of $R^d$. In some aspects of these embodiments, $R^d$ is halo (e.g., fluorine or chlorine). In some aspects of these embodiments, $R^d$ is —C(O)OR$^a$. In some aspects of these embodiments, $R^a$ is alkyl (e.g., methyl or ethyl). In some aspects of these embodiments, L is —NHC(O)—.

In some embodiments, $R^1$ is alkyl substituted with 2 occurrences of $R^d$ (e.g., methyl, ethyl, n-propyl, i-propyl, or n-butyl). In some embodiments, $R^1$ is methyl, ethyl, or n-propyl substituted with 2 occurrences of $R^d$. In some embodiments, $R^1$ is n-propyl substituted with 2 occurrences of $R^d$. In some aspects of these embodiments, 1 $R^d$ is cyano and the other $R^d$ is —NR$^a$R$^b$. In some aspects of these embodiments, le and $R^b$ are hydrogen. In some aspects of these embodiments, L is —$CH_2$—.

In some embodiments, $R^1$ is heteroaryl substituted with 0-5 occurrences of $R^d$ (e.g., S-containing monocyclic heteroaryl, N-containing monocyclic heteroaryl or N-containing bicyclic heteroaryl). In some embodiments, $R^1$ is a 5-8 membered monocyclic heteroaryl substituted with 0-5 occurrences of $R^d$ (e.g., thiophenyl, pyridyl, pyrimidyl or pyrazyl). In some embodiments, $R^1$ is pyridyl substituted with 0-5 occurrences of $R^d$ (e.g., 2-pyridyl, 3-pyridyl or 4-pyridyl), pyrimidyl substituted with 0-5 occurrences of $R^d$ (e.g., 2-pyrimidyl or 5-pyrimidyl) or pyrazinyl substituted with 0-5 occurrences of $R^d$ (e.g., 2-pyrazinyl). In some embodiments, $R^1$ is thiazolyl substituted with 0-5 occurrences of $R^d$ (e.g., 2-thiazolyl or 5-thiazolyl). In some embodiments, $R^1$ is pyrimidyl substituted with 0-5 occurrences of $R^d$ (e.g., 2-pyrimidyl). In some embodiments, $R^1$ is thiadiazolyl substituted with 0-5 occurrences of $R^d$ (e.g., 4-thiadiazolyl). In some embodiments, $R^1$ is pyrrolyl substituted with 0-5 occurrences of $R^d$ (e.g., 2-pyrrolyl). In some aspects of these embodiments, L is a bond, —$CH_2$—, —C(O)—, or —O(CO)—. In some embodiments, $R^1$ is pyridyl (e.g., 2-pyridyl, 3-pyridyl or 4-pyridyl).

In some embodiments, $R^1$ is pyridyl (e.g., 2-pyridyl, 3-pyridyl or 4-pyridyl) substituted with 1 occurrence of $R^d$. In some aspects of these embodiments, $R^d$ is —OC(O)R$^a$. In some aspects of these embodiments, $R^d$ is —OR$^a$. In some aspects of these embodiments, $R^d$ is —C(O)OR$^a$. In some aspects of these embodiments, $R^d$ is alkyl (e.g., methyl or ethyl). In some aspects of these embodiments, $R^d$ is haloalkyl (e.g., trifluoromethyl). In some aspects of these embodiments, $R^d$ is halo (e.g., fluorine or chlorine). In some aspects of these embodiments, $R^a$ is alkyl (e.g., methyl or ethyl). In some aspects of these embodiments, L is —$CH_2$—. In some embodiments, $R^1$ is pyridyl (e.g., 2-pyridyl, 3-pyridyl or 4-pyridyl) substituted with 2 occurrences of $R^d$. In some aspects of these embodiments, one $R^d$ is —C(O)OR$^a$ and the other $R^d$ is —OR$^a$. In some aspects of these embodiments, $R^a$ is alkyl (e.g., methyl or ethyl). In some aspects of these embodiments, both $R^d$ are halo (e.g., fluoro or chloro). In some aspects of these embodiments, L is —$CH_2$—.

In some embodiments, $R^1$ is pyrimidyl (e.g., 2-pyrimidyl or 5-pyrimidyl). In some aspects of these embodiments, L is a bond.

In some embodiments, $R^1$ is pyrimidyl (e.g., 2-pyrimidyl or 5-pyrimidyl) substituted with 1 occurrence of $R^d$. In some aspects of these embodiments, $R^d$ is halo (e.g., fluoro or chloro).

In some embodiments, $R^1$ is pyrazinyl (e.g., 2-pyrazinyl). In some aspects of these embodiments, L is a bond.

In some embodiments, $R^1$ is thiazolyl (e.g., 2-thiazolyl, 4-thiazolyl, or 5-thiazolyl). In some aspects of these embodiments, L is —C(O)—.

In some embodiments, $R^1$ is thiazolyl (e.g., 2-thiazolyl, 4-thiazolyl, or 5-thiazolyl) substituted with 1 occurrences of $R^d$. In some aspects of these embodiments, $R^d$ is alkyl (e.g, methyl or ethyl). In some aspects of these embodiments, L is —C(O)—.

In some embodiments, $R^1$ is thiophenyl substituted with 0-5 occurrences of $R^d$ (e.g., 2-thiophenyl). In some embodiments, $R^1$ is thiophenyl.

In some embodiments, $R^1$ is thiadiazolyl (e.g., 4-thiadiazolyl).

In some embodiments, $R^1$ is pyrrolyl (e.g., 2-pyrrolyl).

In some embodiments, $R^1$ is cycloalkyl substituted with 0-5 occurrences of $R^d$ (e.g., cyclopropyl, cyclopentyl or cyclohexyl). In some embodiments, $R^1$ is cyclopropyl. In some embodiments, $R^1$ is cyclohexyl. In some embodiments, $R^1$ is cyclopentyl. In some aspect of these embodiments, L is —$CH_2$—C(O)—. In some embodiment, $R^1$ is aryl substituted with 0-5 occurrences of $R^d$. In some aspects of these embodiments, L is a bond, —$CH_2$—, —C(O)—, or —O(CO)—.

In some embodiments $R^1$ is aryl (e.g., phenyl). In some embodiments, $R^1$ is phenyl. In some aspects of these embodiments, L is a bond, —$CH_2$—, —C(O)—, or —O(CO)—.

In some embodiments, $R^1$ is phenyl substituted with 1 occurrence of $R^d$. In some aspects of these embodiments, $R^d$ is ortho substituted. In some aspects of these embodiments, $R^d$ is meta substituted. In some aspects of these embodiments, $R^d$ is para substituted. In some aspects of these embodiments, $R^d$ is halo (e.g., fluorine, bromine or chlorine). In some aspects of these embodiments, $R^d$ is alkyl (e.g., methyl, ethyl, isopropyl, t-butyl, n-butyl or n-pentyl). In some aspects of these embodiments, $R^d$ is haloalkyl (e.g., trifluoromethyl). In some aspects of these embodiments, $R^d$ is —OR$^a$. In some aspects of these embodiments, $R^d$ is —C(O)R$^a$. In some aspects of these embodiments, $R^d$ is —SR$^a$. In some aspects of these embodiments, $R^d$ is —C(O)OR$^a$. In some aspects of these embodiments, $R^d$ is cyano. In some aspects of these embodiments, $R^d$ is —NR$^a$R$^b$. In some aspects of these embodiments, $R^d$ is haloalkoxy (e.g., difluoromethoxy or trifluoromethoxy). In some aspects of these embodiments, $R^d$ is hydroxyl. In some aspects of these embodiments, $R^d$ is —OC(O)R$^a$. In some aspects of these embodiments, $R^d$ is alkynyl (e.g., 1-hexynyl). In some aspects of these embodiments, $R^d$ is haloalkyl (e.g., trifluoromethyl). In some aspects of these embodiments, $R^a$ is alkyl (e.g., methyl, ethyl, n-propyl, isopropyl, n-butyl, isobutyl, t-butyl or n-pentyl). In some aspects of these embodiments, $R^a$ is hydroxyalkyl (e.g., 2-hydroxylethyl). In some aspects of these embodiments, $R^a$ and $R^b$ are alkyl (e.g., methyl or ethyl). In some aspects of these embodiments, $R^a$ is acyl (e.g., acetyl) and $R^b$ is hydrogen. In some aspects of these embodiments, L is a bond, —$CH_2$—, —C(O)—, or —O(CO)—.

In some embodiments, $R^1$ is phenyl substituted with 2 occurrences of $R^d$. In some aspects of these embodiments, both $R^d$ are halo (e.g., fluorine or chlorine). In some aspects of these embodiments, both $R^d$ are alkyl (e.g., methyl or ethyl). In some aspects of these embodiments, 1 $R^d$ is alkyl (e.g., methyl or ethyl) and the other is —$OR^a$. In some aspects of these embodiments, 1 $R^d$ is halo (e.g., fluorine or chlorine) and the other $R^d$ is —$OR^a$. In some aspects of these embodiments, both $R^d$ are —$OR^a$. In some aspects of these embodiments, 1 $R^d$ is halo (e.g., fluorine or chlorine) and the other $R^d$ is hydroxyl. In some aspects of these embodiments, 1 $R^d$ is halo (e.g., fluorine or chlorine) and the other is haloalkyl (e.g., trifluoromethyl). In some aspects of these embodiments, 1 $R^d$ is —$OR^a$ and the other $R^d$ is —C(O)$OR^a$. In some aspects of these embodiments, 1 $R^d$ is —$OR^a$ and the other $R^d$ is hydroxyl. In some aspects of these embodiments, 1 $R^d$ is alkyl (e.g., methyl or ethyl) and the other $R^d$ is hydroxyl. In some aspects of these embodiments, both $R^d$ are hydroxyl. In some aspects of these embodiments, 1 $R^d$ is halo (e.g., fluorine) and the other $R^d$ is haloalkyl (e.g., trifluoromethyl). In some aspects of these embodiments, both $R^d$ are hydroxyl. In some aspects of these embodiments, one $R^d$ is haloalkyl (e.g., trifluoromethyl) and the other $R^d$ is alkyl (e.g., methyl). In some aspects of these embodiments, two $R^d$, together with the carbon atoms to which they are attached, form an optionally substituted heterocyclyl. In some aspects of these embodiments, two $R^d$, together with the carbon atoms to which they are attached, form an optionally substituted 5-7 membered heterocyclyl. In some aspects of these embodiments, two $R^d$, together with the phenyl ring to which they are attached, form the following structure:

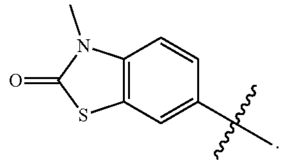 [SMILES: *c1ccc2c(c1)sc(=O)n2C]

In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is phenyl substituted with 3 occurrences of $R^d$. In some aspects of these embodiments, 3 $R^d$ are halo (e.g., fluorine or chlorine). In some aspects of these embodiments, 2 $R^d$ are halo (e.g., fluorine or chlorine) and 1 $R^d$ is hydroxyl. In some aspects of these embodiments, 1 $R^d$ is halo (e.g., fluorine or chlorine), 1 $R^d$ is alkyl (e.g., methyl) and 1 $R^d$ is hydroxyl. In some aspects of these embodiments, 3 $R^d$ are alkyl (e.g., methyl or ethyl). In some aspects of these embodiments, 2 $R^d$ are alkyl (e.g., methyl or ethyl) and 1 $R^d$ is hydroxyl. In some aspects of these embodiments, 2 $R^d$ are halo (e.g., fluorine or chlorine) and 1 $R^d$ is —$OR^a$. In some aspects of these embodiments, $R^a$ is alkyl (e.g., methyl or ethyl). In some aspects of these embodiments, 1 $R^d$ is hydroxyl and 2 $R^d$ are —$OR^a$. In some aspects of these embodiments, $R^a$ is alkyl (e.g., methyl or ethyl). In some aspects of these embodiments, 3 $R^d$ are —$OR^a$. In some aspects of these embodiments, 3 $R^d$ are halo (e.g., fluorine or chlorine). In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is phenyl substituted with 4 occurrences of $R^d$. In some aspects of these embodiments, 1 $R^d$ is hydroxyl, 1 $R^d$ is alkyl (e.g., methyl or ethyl) and 2 $R^d$ are —$OR^a$. In some aspects of these embodiments, $R^a$ is alkyl (e.g., methyl or ethyl). In some aspects of these embodiments, L is a bond, —$CH_2$—, —C(O)—, or —O(CO)—.

In some embodiments, $R^1$ is heterocyclyl substituted with 0-5 occurrences of $R^d$.

In some embodiments, $R^1$ is tetrahydrofuranyl substituted with 0-5 occurrences of $R^d$ (e.g., 2-tetrahydrofuranyl or 3-tetrahydrofuranyl). In some aspects of these embodiments, $R^1$ is tetrahydrofuranyl (e.g., 2-tetrahydrofuranyl or 3-tetrahydrofuranyl). In some aspects of these embodiments, L is —C(O)—.

In some embodiments, $R^1$ is azetidinyl substituted with 0-5 occurrences of $R^d$ (e.g., 3-azetidinyl). In some embodiments, $R^1$ is azetidinyl (e.g., 3-azetidinyl). In some embodiments, $R^1$ is azetidinyl (e.g., 3-azetidinyl) substituted with 1 occurrence of $R^d$. In some aspects of these embodiments, $R^d$ is alkyl (e.g., methyl or ethyl). In some aspects of these embodiments, L is —C(O)—.

In some embodiments, $R^1$ is 10-14 membered bicyclic aryl substituted with 0-5 occurrences of $R^d$. In some embodiments, $R^d$ is naphthyl substituted with 0-5 occurrences of $R^d$. In some embodiments, $R^d$ is naphthyl.

In some embodiments, L is a bond, —$(CR^cR^c)_m$—, —$NR^bC(O)$—, —$(CR^cR^c)_m$—C(O)—, —C(O)—, or —O(CO)—.

In some embodiments, L is a bond and $R^1$ is alkyl, aryl or heteroaryl substituted with 0-5 occurrences of $R^d$. In some aspects of these embodiments, alkyl, aryl or heteroaryl of $R^1$ is as described in any one of the embodiments and aspects above.

In some embodiments, L is —$(CR^cR^c)_m$— and $R^1$ is cycloalkyl, aryl, heteroaryl or heterocyclyl substituted with 0-5 occurrences of $R^d$. In some aspects of these embodiments, cycloalkyl, aryl, heteroaryl or heterocyclyl of $R^1$ is as described in any one of the embodiments and aspects above.

In some embodiments, L is —$NR^bC(O)$— and $R^b$ is hydrogen; and $R^1$ is aryl substituted with 0-5 occurrences of $R^d$. In some aspects of these embodiments, aryl of $R^1$ is as described in any one of the embodiments and aspects above.

In some embodiments, L is —$(CR^cR^c)_m$—C(O)— and $R^1$ is cycloalkyl, aryl or heteroaryl substituted with 0-5 occurrences of $R^d$. In some aspects of these embodiments, cycloalkyl, aryl, or heteroaryl of $R^1$ is as described in any one of the embodiments and aspects above.

In some embodiments, L is —C(O)— and $R^1$ is aryl, alkyl, or heteroaryl substituted with 0-5 occurrences of $R^d$. In some aspects of these embodiments, aryl, alkyl, or heteroaryl of $R^1$ is as described in any one of the embodiments and aspects above.

In some embodiments, L is —OC(O)— and $R^1$ is alkyl, aryl or heterocyclyl substituted with 0-5 occurrences of $R^d$. In some aspects of these embodiments, alkyl, aryl, or heterocyclyl of $R^1$ is as described in any one of the embodiments and aspects above.

In some embodiments, L is —$(CR^cR^c)_m$—OC(O)— and $R^1$ is heterocyclyl or cycloalkyl substituted with 0-5 occurrences of $R^d$. In some aspects of these embodiments, heterocyclyl or cycloalkyl of $R^1$ is as described in any one of the embodiments and aspects above.

In some embodiments, n is 0. In some embodiments, n is 1.

In some embodiments, $R^3$ is alkyl (e.g., methyl or ethyl). In some embodiments, $R^3$ is —$OR^a$. In some aspects of these embodiments, $R^a$ is alkyl (e.g., methyl or ethyl). In some embodiments, $R^3$ is halo (e.g., fluorine or chlorine). In some embodiments, $R^3$ is hydroxyl. In some embodiments, $R^3$ is haloalkyl (e.g., trifluoromethyl).

In some embodiments, n is 2.

In some embodiments, two adjacent $R^3$ taken together with the carbon atoms to which they are attached form a heterocyclyl ring. In some embodiments, both $R^3$ are —$OR^a$. In some embodiments, two adjacent $R^3$ taken together with the carbon atoms to which they are attached form

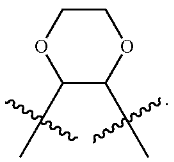 [SMILES: *C1OCCOC1*]

In certain embodiments, a compound is of formula (II) or a pharmaceutical acceptable salt thereof:

(II)

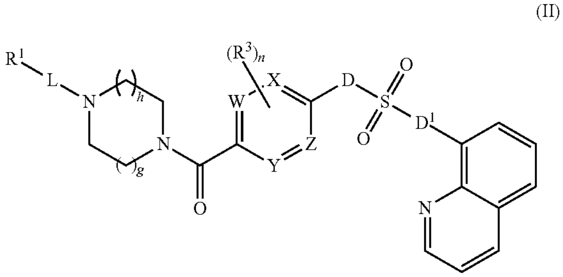

wherein L, $R^1$, $R^3$, $R^a$, $R^b$, $R^c$, $R^d$, Y, Z, m, h and g are as defined above in formula (I) or any one of the embodiments or aspects described herein.

In certain embodiments, A is aryl (e.g., phenyl or naphthyl) optionally substituted with 1 or 2 occurrences of $R^2$, wherein each $R^2$ is independently selected from halo, haloalkyl, aryl, heteroaryl, alkyl, —$OR^a$, —$COOR^c$, or —$CONR^cR^c$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspect of these embodiments, D and $D^1$ are N. In some aspect of these embodiments, at least one of W, X, Y and Z is N. In some aspect of these embodiments, one of W, Y and Z is N; h is 1 and g is 1.

In certain embodiments, A is heteroaryl (e.g., N-containing monocyclic heteroaryl or N-containing bicyclic heteroaryl); and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is a 5-8 membered monocyclic heteroaryl (e.g., pyridyl, pyrimidyl, or pyrazyl); and D, $D^1$, L, $R^1$, $R^3$, $R^a$, $R^b$, R X, Y, Z, W, n, m, h and g are as defined above in formula (I) or any one of the embodiments or aspects described herein. In some embodiments, A is a 5-8 membered N-containing monocyclic heteroaryl; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some embodiments, A is optionally substituted pyridyl (e.g., 2-pyridyl, 3-pyridyl or 4-pyridyl), optionally substituted pyrimidyl (e.g., 2-pyrimidyl or 5-pyrimidyl), or optionally substituted pyrazyl (e.g., 2-pyrazyl); and L, $R^1$, $R^3$, $R^a$, $R^b$, R Y, Z, m, h and g are as defined above in formula (I) or any one of the embodiments or aspects described herein.

In some embodiments, A is substituted with 1 occurrence of $R^2$; and D, $D^1$, L, $R^1$, $R^3$, $R^a$, $R^b$, R X, Y, Z, W, n, m, h and g are as defined above in formula (I) or any one of the embodiments or aspects described herein. In some aspects of these embodiments, $R^2$ is alkyl (e.g., methyl or ethyl). In some aspects of these embodiments, $R^2$ is halo. In some aspects of these embodiments, $R^2$ is fluorine (F). In some aspects of these embodiments, $R^2$ is bromine (Br). In some aspects of these embodiments, $R^2$ is chlorine (Cl). In some aspects of these embodiments, $R^2$ is —$OR^a$. In some aspects of these embodiments, $R^a$ is alkyl (e.g., methyl).

In some embodiments, A is substituted with 2 occurrences of $R^2$; and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein. In some aspects of these embodiments, both $R^2$ are halo (e.g., fluorine or fluorine and chlorine). In some aspects of these embodiments, both $R^2$ are alkyl (e.g, methyl). In some aspects of these embodiments, both $R^2$ are —$OR^a$. In some aspects of these embodiments, one $R^2$ is halo and the other is —$OR^a$. In some aspects of these embodiments, one $R^2$ is bromine (BR) and the other is —$OR^a$. In some aspects of these embodiments, one $R^2$ is chlorine (Cl) and the other is —$OR^a$. In some aspects of these embodiments, one $R^2$ is fluorine (F) and the other is —$OR^a$. In some aspects of these embodiments, $R^a$ is alkyl (e.g., methyl or ethyl). In some aspects of these embodiments, both $R^2$ are —$OR^a$. In some aspects of these embodiments, two —$OR^a$ taken together with the carbon atoms to which they are attached form a heterocyclyl. In some embodiments, A is

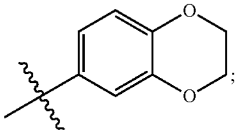 [SMILES: *c1ccc2c(c1)OCCO2];

and D, $D^1$, L, $R^1$, $R^3$, $R^a$, $R^b$, $R^c$, $R^d$, X, Y, Z, W, n, m, h and g are as defined above in formula (I) or any one of the embodiments or aspects described herein.

In another embodiment, provided is a compound of formula (I) or a pharmaceutically acceptable salt thereof, or a pharmaceutical composition comprising a compound of formula (I) or a pharmaceutically acceptable salt thereof:

(I)

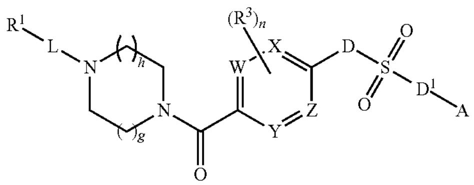

wherein:

W, X, Y and Z are each independently selected from CH or N;

D and $D^1$ are independently selected from a bond or $NR^b$;

A is optionally substituted aryl or optionally substituted heteroaryl;

L is a bond, —C(O)—, —$(CR^cR^c)_m$—, —OC(O)—, or —$C(O)NR^b$—;

$R^1$ is independently selected from alkyl, cycloalkyl, aryl, heteroaryl, and heterocyclyl; each of which are substituted with 0-3 occurrences of $R^d$;

each $R^3$ is independently selected from halo, haloalkyl, alkyl, hydroxyl and —$OR^a$ or two adjacent $R^3$ taken together with the carbon atoms to which they are attached form an optionally substituted cyclyl;

each $R^a$ is independently selected from alkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, alkyl, nitro, cyano and —$OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2. In some aspects of this embodiment, A, D, $D^1$, L, $R^1$, $R^3$, $R^a$, $R^b$, $R^c$, $R^d$, X, Y, Z, W, n, m, h and g are as defined in any one of the embodiments or aspects described herein.

In another embodiment, provided is a compound of formula (I) or a pharmaceutically acceptable salt thereof, or a pharmaceutical composition comprising a compound of formula (I) or a pharmaceutically acceptable salt thereof:

(I)

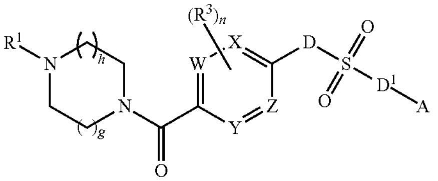

wherein:

W, X, Y and Z are each independently selected from CH or N;

D and $D^1$ are independently selected from a bond or $NR^c$;

A is optionally substituted aryl or optionally substituted heteroaryl;

$R^1$ is independently selected from alkyl, optionally substituted aryl, and optionally substituted heteroaryl;

each $R^3$ is independently selected from halo, haloalkyl, alkyl, and —$OR^a$;

each $R^a$ is independently selected from alkyl, haloalkyl and optionally substituted heteroaryl;

each $R^b$ is independently alkyl;

each $R^c$ is independently selected from hydrogen or alkyl;

n is 0, 1, or 2;

h is 0, 1, 2; and g is 0, 1 or 2. In some aspects of this embodiment, A, D, $D^1$, L, $R^1$, $R^3$, $R^a$, $R^b$, $R^c$, $R^d$, X, Y, Z, W, n, m, h and g are as defined in any one of the embodiments or aspects described herein.

In another embodiment, provided is a compound or pharmaceutically acceptable salt of formula (Ib) or a pharmaceutical composition comprising a compound or pharmaceutically acceptable salt of formula (Ib):

(Ib)

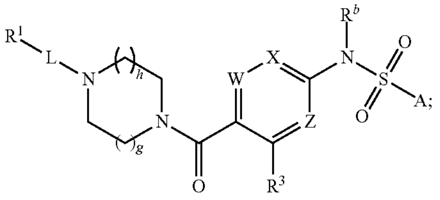

wherein A, L, $R^1$, $R^3$, $R^a$, $R^b$, $R^c$, $R^d$, W, X, Z, m, h and g are as defined above in formula (I) or any one of the embodiments or aspects described herein.

In some embodiments, X, W and Z are CH. In some embodiments, one of X, W and Z is N and the other two of X, W and Z are CH.

In another embodiment, provided is a pharmaceutical composition comprising a compound or pharmaceutically acceptable salt of formula (Ic) or a pharmaceutical composition comprising a compound or pharmaceutically acceptable salt of formula (Ic):

(Ic)

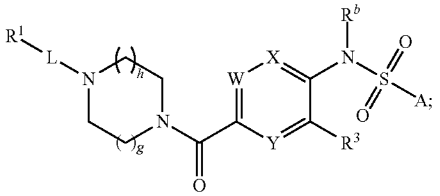

wherein A, L, $R^1$, $R^3$, $R^a$, $R^b$, $R^c$, $R^d$, W, X, Y, m, h and g are as defined above in formula (I) or any one of the embodiments or aspects described herein.

In some embodiments, X, Y and W are CH. In some embodiments, one of X, Y and W is N and the other two of X, Y and W are CH.

In another embodiment, provided is a compound or pharmaceutically acceptable salt of formula (Id) or a pharmaceutical composition comprising a compound or pharmaceutically acceptable salt of formula (Id):

(Id)

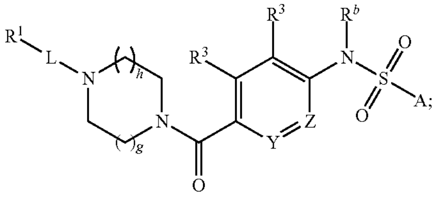

wherein A, L, $R^1$, $R^3$, $R^a$, $R^b$, $R^c$, $R^d$, Y, Z, m, h and g are as defined above in formula (I) or any one of the embodiments or aspects described herein.

In some embodiments, Y and Z are CH. In some embodiments, one of Y and Z is N and one of Y and Z is CH.

In another embodiment, provided is a compound or pharmaceutically acceptable salt of formula (Ie) or a pharmaceutical composition comprising a compound or pharmaceutically acceptable salt of formula (Ie):

(Ie)

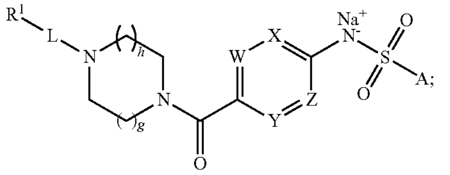

wherein A, L, $R^1$, $R^3$, $R^a$, $R^b$, $R^c$, $R^d$, W, X, Y, Z, m, h and g are as defined above in formula (I) or any one of the embodiments or aspects described herein.

In certain embodiments, exemplary compounds of Formula I include the compounds described in FIG. 1 and in the Examples.

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 1. Compounds described herein are also useful as activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2, 3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

A compound described herein may be an activator of a PKR, for example, a wild type (wt) or mutated PKR (e.g., R510Q, R532W, OR T384W). Exemplary compounds are shown in FIG. 1. As shown in FIG. 1, A refers to a compound that has a % activation at 1 μM of from 1 to 100. B refers to an a compound that has a % activation at 1 μM of from 101 to 500. C refers a compound that has a % activation at 1 μM of >500.

In FIG. 1, a compound described herein may also have an AC50 of wild type PKR, PKR R532W, PKR T384W, PKR G332S, PKR G364D, PKR G37E and/or PKR R479H. AA refers to an AC50 less than 100 nM, BB refers to an AC50 from 101 nM to 500 nM and CC refers to an AC50 greater than 500 nM.

Other exemplary compounds can be found in International Patent Application No. PCT/US2010/040486 (e.g., in FIG. 1), published as WO 2011/002817 which is incorporated herein by reference in its entirety.

The compounds described herein can be made using a variety of synthetic techniques.

Scheme 1.

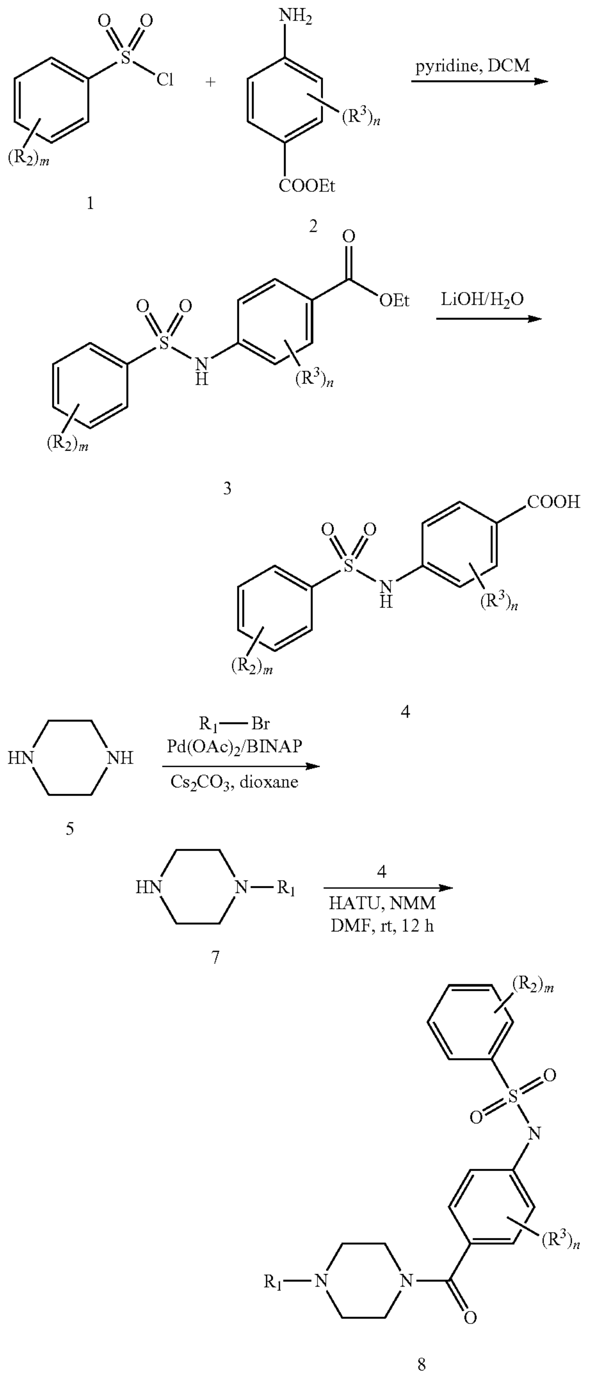

$R^1$, $R^2$, $R^3$, m and n = as defined herein

Scheme 1 above is an exemplary scheme that depicts a representative synthesis of certain compounds described herein. Sulfonyl chloride 1 is reacted with amine 2 under standard coupling conditions to produce ester 3. Hydrolysis of 3 using lithium hydroxide generates carboxylic acid 4. Piperazine (5) is with the appropriate bromide under standard palladium coupling conditions to provide 7. Carboxylic acid 4 is then treated with piperazine derivative 7 to produce final compound 8.

The compounds described herein can be made using procedures disclosed in International Patent Application No. PCT/US2010/040486, published as WO 2011/002817 which is incorporated herein by reference in its entirety.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g. restriction resulting from the presence of a ring or double bond. Accordingly, all cis/trans and E/Z isomers are expressly included.

The compounds provided herein (e.g. of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., $—CH_2—$, $—CH_2CH_2—$, and $—CH_2CH_2CH_2—$.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The terms "alkylamino" and "dialkylamino" refer to —NH(alkyl) and $—NH(alkyl)_2$ radicals respectively. The term "aralkylamino" refers to a —NH(aralkyl) radical. The term alkylaminoalkyl refers to a (alkyl)NH-alkyl-radical; the term dialkylaminoalkyl refers to a $(alkyl)_2N$-alkyl-radical The term "alkoxy" refers to an —O-alkyl radical. The term "mercapto" refers to an SH radical. The term "thioalkoxy" refers to an —S-alkyl radical. The term thioaryloxy refers to an —S-aryl radical.

The term "aryl" refers to a monocyclic, bicyclic, or tricyclic aromatic hydrocarbon ring system, wherein any ring atom capable of substitution can be substituted (e.g., by one or more substituents). Examples of aryl moieties include, but are not limited to, phenyl, naphthyl, and anthracenyl.

The term "cycloalkyl" as employed herein includes cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings.

Fused rings are rings that share a common carbon atom. Examples of cycloalkyl moieties include, but are not limited to, cyclopropyl, cyclohexyl, methylcyclohexyl, adamantyl, and norbornyl.

The terms "heterocyclyl" or "heterocyclic group" refer to 3- to 14-membered non-aromatic ring structures (e.g., 3- to 14-membered rings, more preferably 3- to 7-membered rings), whose ring structures include one to four heteroatoms independently selected from O, N and S. The heterocyclyl or heterocyclic groups can contain fused or spiro rings. Heterocycles can also be polycycles, with each group having, e.g., 5-7 ring members. The term "heterocyclyl" or "heterocyclic group" includes saturated and partially saturated heterocyclyl structures. The term "heteroaryl" refers to a 5-14 membered (i.e., a 5-8 membered monocyclic, 8-12 membered bicyclic, or 11-14 membered tricyclic) aromatic ring system having 1-3 ring heteroatoms if monocyclic, 1-6 ring heteroatoms if bicyclic, or 1-9 ring heteroatoms if tricyclic, said ring heteroatoms independently selected from O, N, and S (e.g., 1-3, 1-6, or 1-9 ring heteroatoms of N, O, or S if monocyclic, bicyclic, or tricyclic, respectively). Any substitutable ring atom can be substituted (e.g., by one or more substituents). Heterocyclyl and heteroaryl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic or heteroaryl ring can be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, $—CF_3$, —CN, or the like.

The term "heterocyclylalkyl", as used herein, refers to an alkyl group substituted with a heterocycle group.

The term "cycloalkenyl" refers to partially unsaturated, nonaromatic, monocyclic, bicyclic, or tricyclic hydrocarbon groups having 5 to 12 carbons, preferably 5 to 8 carbons. The unsaturated carbon may optionally be the point of attachment of the cycloalkenyl substituent. Any substitutable ring atom can be substituted (e.g., by one or more substituents). The cycloalkenyl groups can contain fused or spiro rings. Fused rings are rings that share a common carbon atom. Examples of cycloalkenyl moieties include, but are not limited to, cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, and S (e.g., 1-3, 1-6, or 1-9 ring heteroatoms of N, O, or S if monocyclic, bicyclic, or tricyclic, respectively). The unsaturated carbon or the heteroatom may optionally be the point of attachment of the heterocycloalkenyl substituent. Any substitutable ring atom can be substituted (e.g., by one or more substituents). The heterocycloalkenyl groups can contain fused rings. Fused rings are rings that share a common carbon atom. Examples of heterocycloalkenyl include but are not limited to tetrahydropyridyl and dihydropyranyl.

The terms "hetaralkyl" and "heteroaralkyl", as used herein, refers to an alkyl group substituted with a heteroaryl group. The ring heteroatoms of the compounds provided herein include N—O, S(O), and $S(O)_2$.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "substituents" refers to a group "substituted" on an alkyl, cycloalkyl, alkenyl, alkynyl, heterocyclyl, heterocycloalkenyl, cycloalkenyl, aryl, or heteroaryl group at any substitutable atom of that group. Any substitutable atom can be substituted. Unless otherwise specified, such substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy ($—O—CH_2—O—$ wherein oxygens are attached to vicinal atoms), ethylenedioxy, oxo (not a substituent on heteroaryl), thioxo (e.g., C═S) (not a substituent on heteroaryl), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

The term "activator" as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain activator compounds useful as PKR wild type and/or mutant activators are those that demonstrate specificity and activation of PKR enzyme (wild type and/or a mutant enzyme) in the absence of FBP to a level greater than that of 10, 15, 20, 25, 30, 35, 40, 45, 50, 55, 60, 65, 70, 75, 80, 85, 90, 95, 99, or 100% in the presence of FBP.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (I-a), (II) or in FIG. 1).

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term “treat” or “treatment” is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a “therapeutically effective amount” refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a “a prophylactically effective amount” of the compound refers to an amount effective, upon single- or multiple-dose administration to the subject, in preventing or delaying the occurrence of the onset or recurrence of a disorder or a symptom of the disorder.

As used herein, the term “subject” is intended to include human and non-human animals. Exemplary human subjects include a human patient having a disorder, e.g., a disorder described herein or a normal subject. The term “non-human animals” includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term “pharmaceutically acceptable carrier or adjuvant” refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer’s solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

Example 1. PKR Mutant Assay

Procedure:

PKR or PKR mutant enzyme solution was diluted in assay buffer.

2 μL of test compound was added into wells first, and then 180 μL reaction mix was added.

Reactions mixture with test compound was assembled except for ADP, and plates were stored for 60 minutes at room temperature.

20 μL ADP was added to start reaction at room temperature and reaction progress was measured as changes in absorbance at 340 nm wavelength at room temperature.

Test Compound Preparation:

Test compound stock was made at 100× concentration in 100% DMSO (10 mM)

1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)

1 to 100 dilution into assay (2 μl in 200 μl) yielded starting concentration of 100 μM, decreasing 3 fold for 11 points.

Assay Buffer:

100 mM KCl, 50 mM Tris 7.5, 5 mM MgCl2, 1 mM DTT, 0.03% BSA

Reaction Mixture:

PKR mutant enzyme: 80-400 ng/well; ADP: 0.22-1.65 mM; PEP: 0.1-0.5 mM; NADH: 180 uM; LDH: 0.5 units (Sigma#59023); DTT: 1 mM; BSA: 0.03%.

Representative compounds disclosed herein were tested to be an activator of wild type PKR, PKRR532W, PKRR479H, and PKRG332S with an AC50 less than 500 nM against each wild type/mutant enzyme.

Example 2. PKR WT Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR wt (100 ng/well), Tris pH 7.5 (50 mM), KCl (100 mM), $MgCl_2$ (5 mM), ADP (0.48 mM), PEP (0.15 mM), NADH (180 μM), LDH (0.5 units, Sigma 59023), DTT (1 mM) and BSA (0.03%).

Example 3. PKR R510Q Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR R510Q (40 ng/well), Tris pH 7.5 (50 mM), KCl (100 mM), $MgCl_2$ (5 mM), ADP (0.2 mM), PEP (0.11 mM), NADH (180 μM), LDH (0.5 units, Sigma 59023), DTT (1 mM) and BSA (0.03%).

Example 4. PKR R532W Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR R532W (100 ng/well), Tris pH 7.5 (50 mM), KCl (100 mM), MgCl2 (5 mM), ADP (0.36 mM), PEP (0.1 mM), NADH (180 μM), LDH (0.5 units, Sigma 59023), DTT (1 mM) and BSA (0.03%).

Example 5. PKR T384W Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR T384W soluble (300 ng/well), Tris pH 7.5 (50 mM), KCl (100 mM), MgCl2 (5 mM), ADP (0.08 mM), PEP (0.23 mM), NADH (180 μM), LDH (0.5 units, Sigma 59023), DTT (1 mM) and BSA (0.03%).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of activating pyruvate kinase R in a subject in need thereof, comprising administering to the subject a therapeutically effective amount of a compound of formula (I) or a pharmaceutically acceptable salt thereof, wherein:

(I)

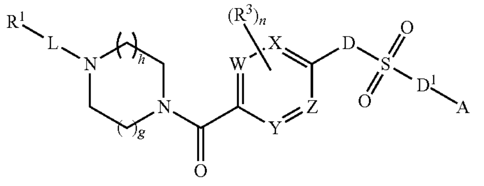

W, X, Y and Z are each independently selected from CH or N;

D and $D^1$ are each independently selected from a bond and $NR^b$;

A is optionally substituted aryl or optionally substituted heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^b$C(S)—, or —$NR^b$C(O)— (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)O$R^a$, —S$R^a$, —$NR^aR^b$ and —$OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2.

2. The method of claim 1, wherein h is 1 and g is 1.

3. The method of claim 2, wherein W, X, Y and Z are CH.

4. The method of claim 3, wherein D is $NR^b$ and $D^1$ is a bond.

5. The method of claim 4, wherein $R^b$ is H, methyl or ethyl.

6. The method of claim 5, wherein L is a bond, —$(CR^cR^c)_m$—, —$NR^bC(O)$—, —$(CR^cR^c)_m$—C(O)—, —C(O)—, or —O(CO)—.

7. The method of claim 6, wherein L is —$(CR^cR^c)_m$—.

8. The method of claim 7, wherein $R^1$ is cycloalkyl, aryl, heteroaryl or heterocyclyl substituted with 0-5 occurrences of $R^d$.

9. The method of claim 8, wherein L is —$CH_2$— and n is 0.

10. The method of claim 1, wherein the compound or a pharmaceutically acceptable salt thereof is selected from:

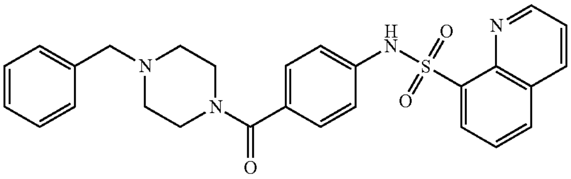,

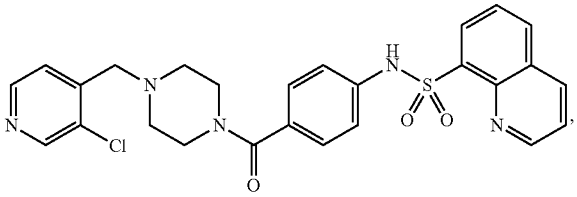,

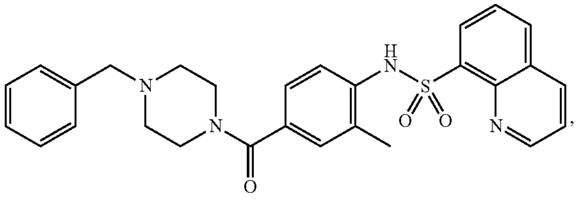,

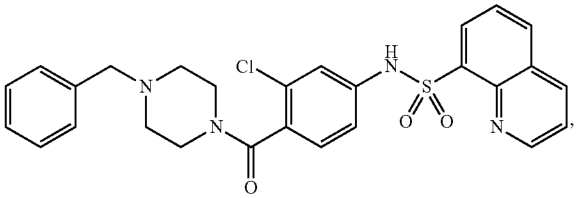,

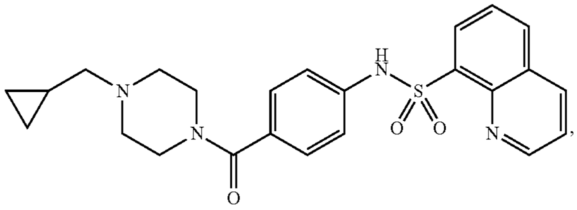,

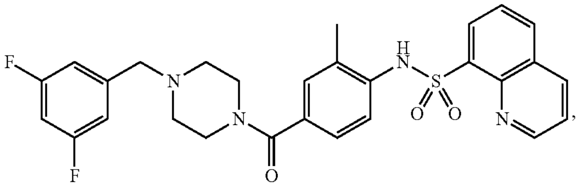,

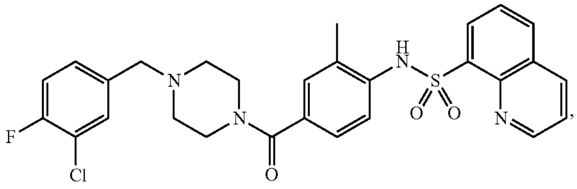,

-continued

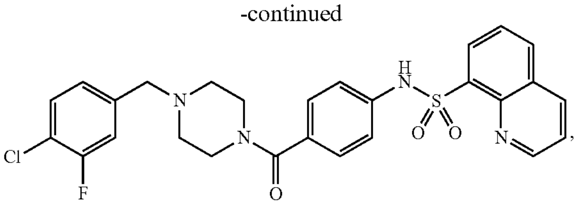,

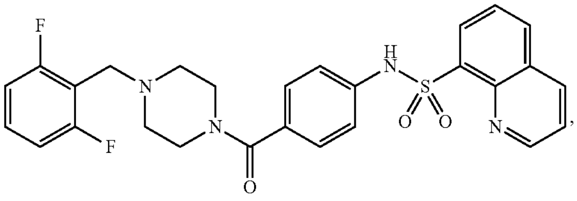,

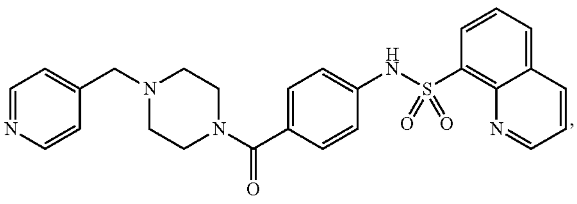,

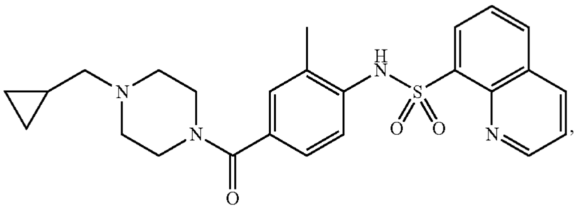,

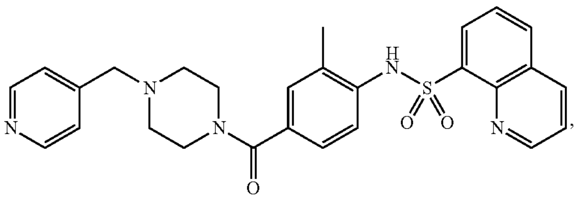,

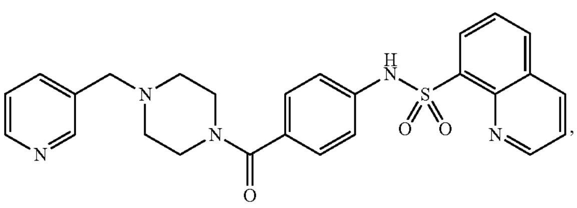,

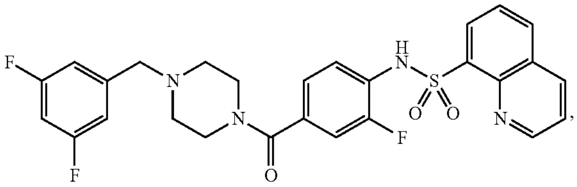,

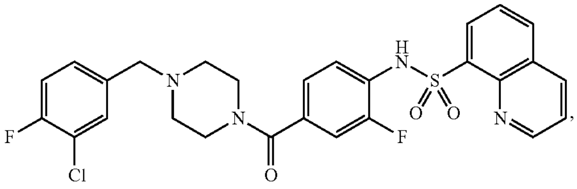,

-continued

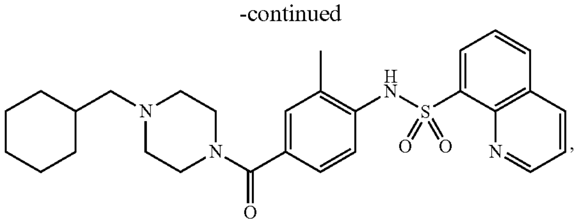
,

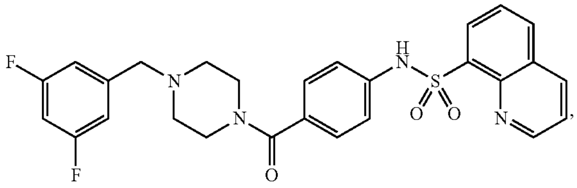
,

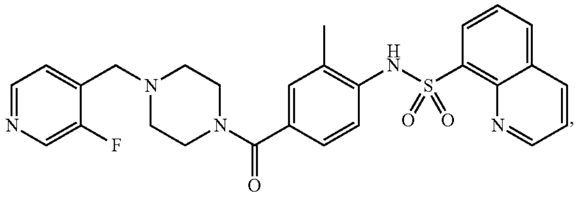
,

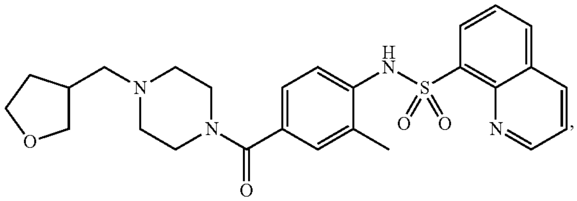
,

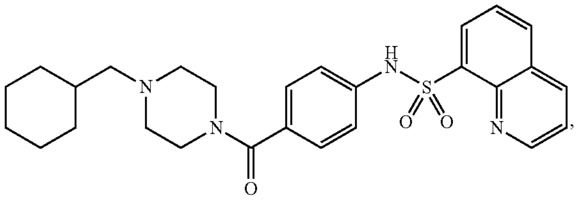
,

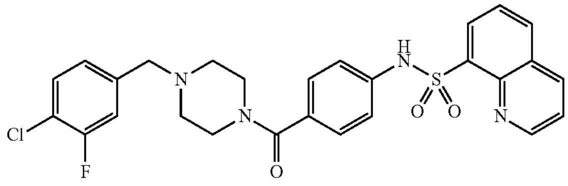
,

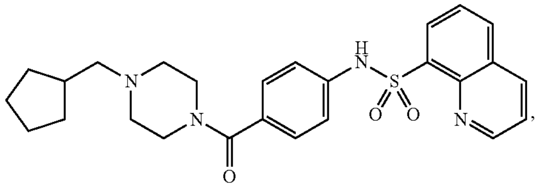
, and

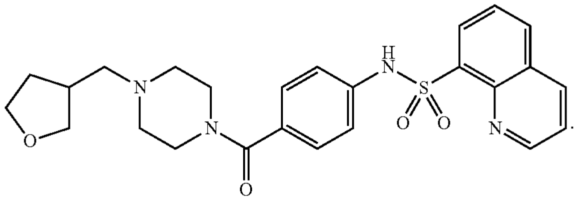
.

11. A method of treating beta-thalassemia in a subject in need thereof, comprising administering to the subject a therapeutically effective amount of a compound of formula I or a pharmaceutically acceptable salt thereof, wherein:

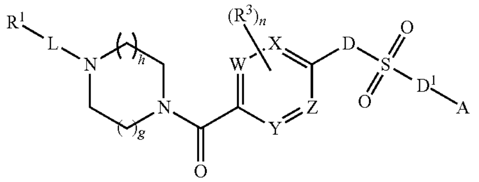
(I)

W, X, Y and Z are each independently selected from CH or N;

D and $D^1$ are each independently selected from a bond and $NR^b$;

A is optionally substituted aryl or optionally substituted heteroaryl;

L is a bond, —C(O)—, $—(CR^cR^c)_m—$, —OC(O)—, $—(CR^cR^c)_m—OC(O)—$, $—(CR^cR^c)_m—C(O)—$, $—NR^bC(S)—$, or $—NR^bC(O)—$ (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and $—OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, $—C(O)R^a$, $—OC(O)R^a$, $—C(O)OR^a$, $—SR^a$, $—NR^aR^b$ and $—OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2.

12. The method of claim 11, wherein h is 1 and g is 1.

13. The method of claim 12, wherein W, X, Y and Z are CH.

14. The method of claim 13, wherein D is $NR^b$ and $D^1$ is a bond.

15. The method of claim 14, wherein $R^b$ is H, methyl or ethyl.

16. The method of claim 15, wherein L is a bond, $—(CR^cR^c)_m—$, $—NR^bC(O)—$, $—(CR^cR^c)_m—$, —C(O)—, —C(O)—, or —O(CO)—.

17. The method of claim 16, wherein L is $—(CR^cR^c)_m—$.

18. The method of claim 17, wherein $R^1$ is cycloalkyl, aryl, heteroaryl or heterocyclyl substituted with 0-5 occurrences of $R^d$.

19. The method of claim 18, wherein L is $—CH_2—$ and n is 0.

20. The method of claim 11, wherein the compound or a pharmaceutically acceptable salt thereof is selected from:

-continued
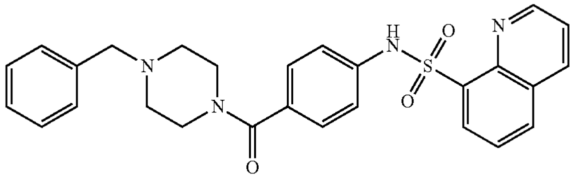,
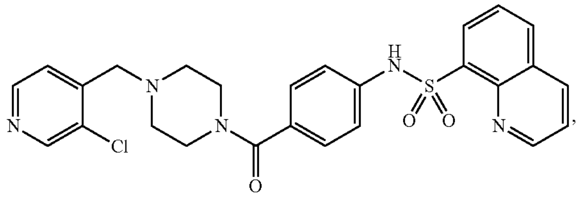,
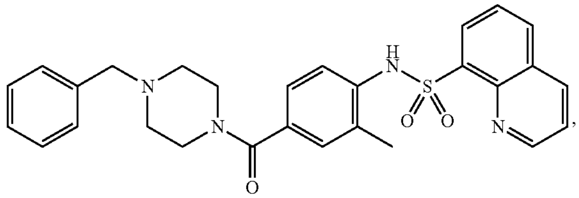,
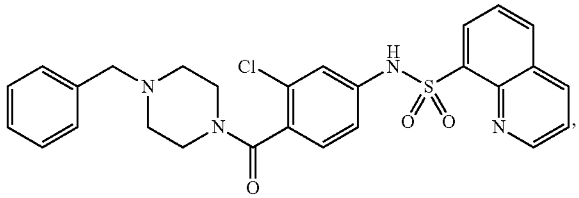,
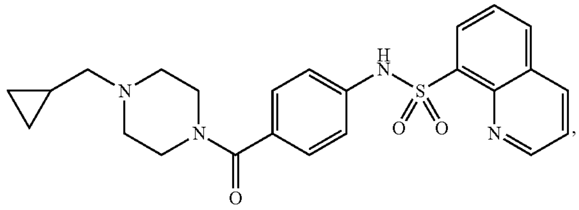,
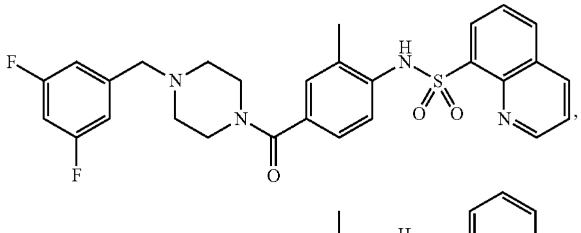,
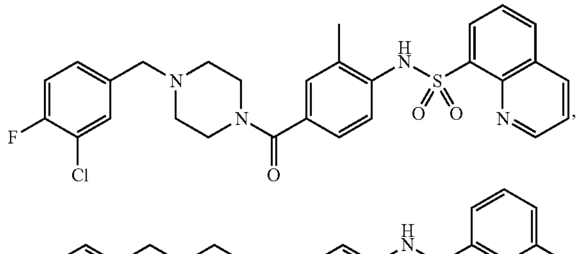,
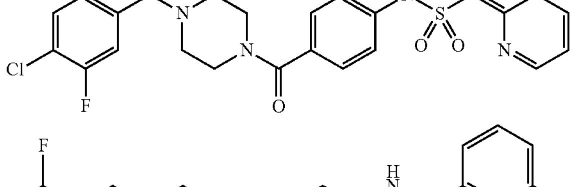,
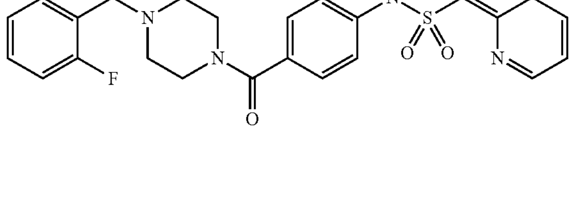,
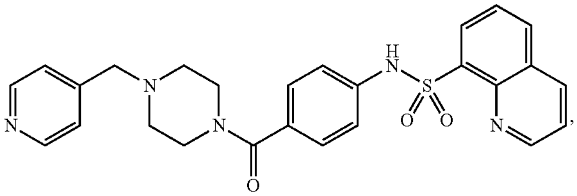,
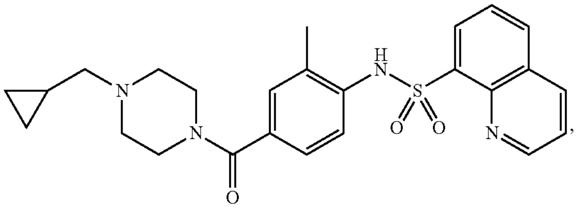,
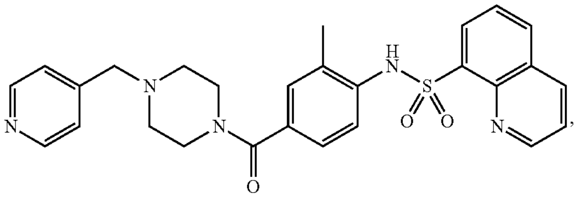,
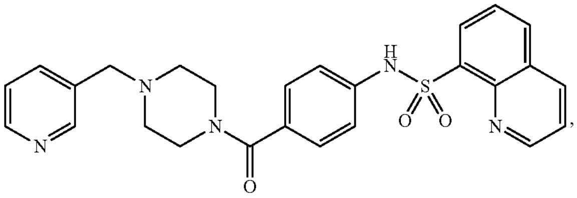,
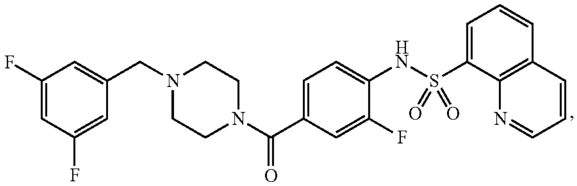,
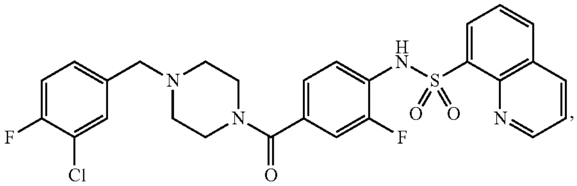,
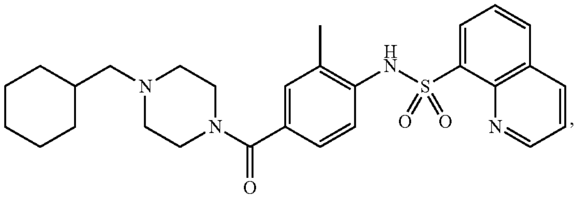,
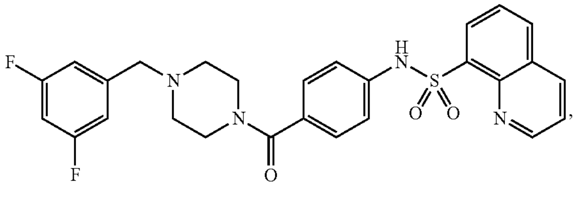, -continued

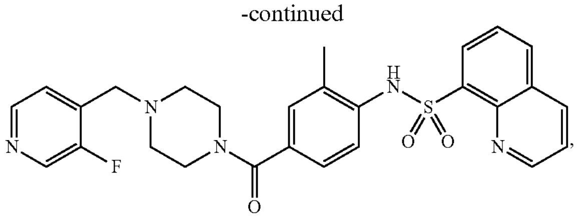,

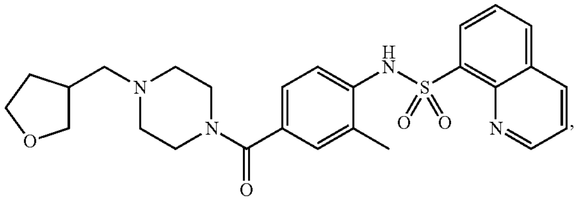,

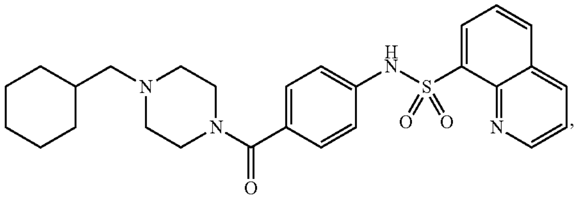,

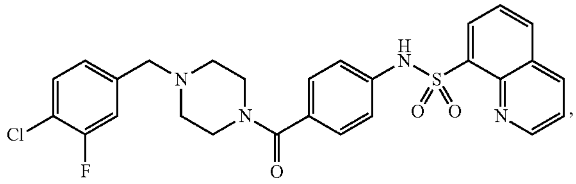,

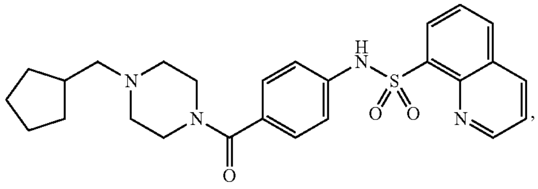, and

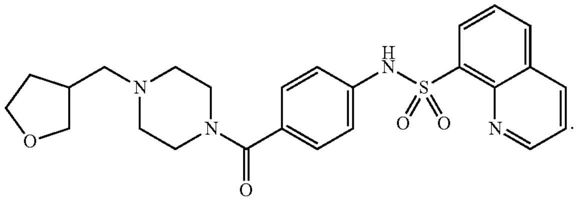.

21. A method of treating sickle cell anemia in a subject in need thereof, comprising administering to the subject a therapeutically effective amount of a compound of formula (Id) or a pharmaceutically acceptable salt thereof, wherein:

(Id)

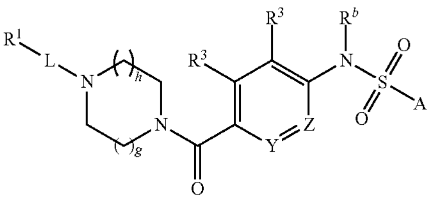

Y and Z are each independently selected from CH or N;

A is optionally substituted aryl or optionally substituted heteroaryl;

L is a bond, —C(O)—, —$(CR^cR^c)_m$—, —OC(O)—, —$(CR^cR^c)_m$—OC(O)—, —$(CR^cR^c)_m$—C(O)—, —$NR^b$C(S)—, or —$NR^b$C(O)— (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and —$OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, —C(O)$R^a$, —OC(O)$R^a$, —C(O)$OR^a$, —$SR^a$, —$NR^aR^b$ and —$OR^a$, or two $R^d$ taken together with the carbon atoms to which they are attached form an optionally substituted heterocyclyl;

m is 1, 2 or 3;

h is 0, 1, 2; and g is 0, 1 or 2.

22. The method of claim 21, wherein h is 1 and g is 1.

23. The method of claim 22, wherein Y and Z are CH.

24. The method of claim 23, wherein $R^b$ is H, methyl or ethyl.

25. The method of claim 24, wherein L is a bond, —$(CR^cR^c)_m$—, —$NR^b$C(O)—, —$(CR^cR^c)_m$—, —C(O)—, —C(O)—, or —O(CO)—.

26. The method of claim 25, wherein L is —$(CR^cR^c)_m$—.

27. The method of claim 26, wherein $R^1$ is cycloalkyl, aryl, heteroaryl or heterocyclyl substituted with 0-5 occurrences of $R^d$.

28. The method of claim 27, wherein L is —$CH_2$— and n is 0.

29. The method of claim 21, wherein the compound or a pharmaceutically acceptable salt thereof is selected from:

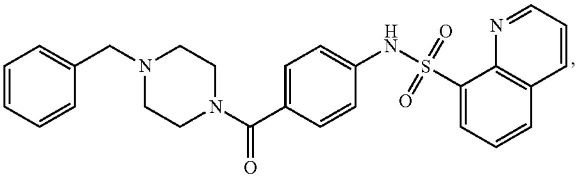,

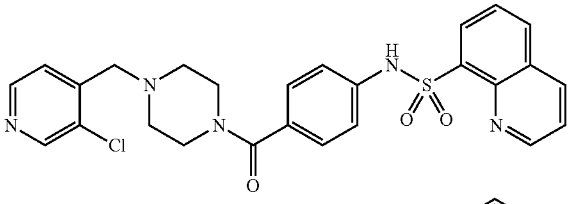,

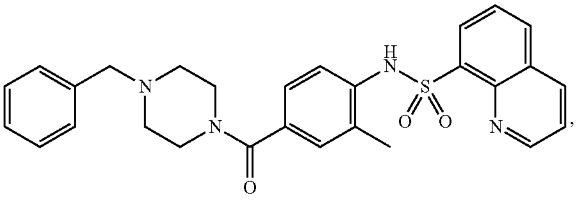,

-continued
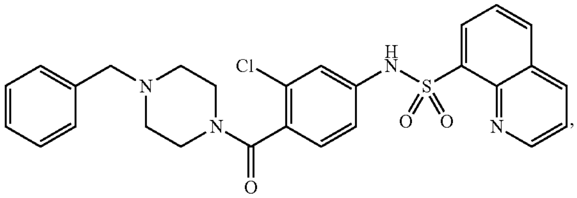,
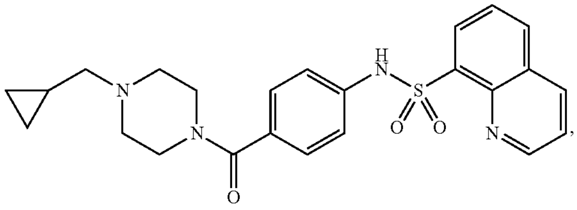,
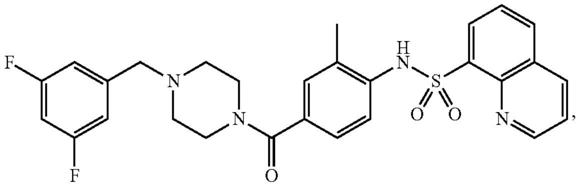,
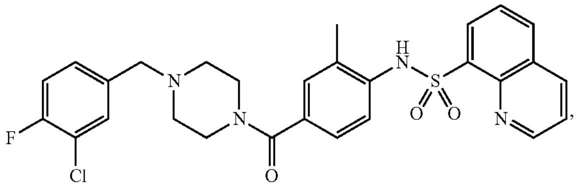,
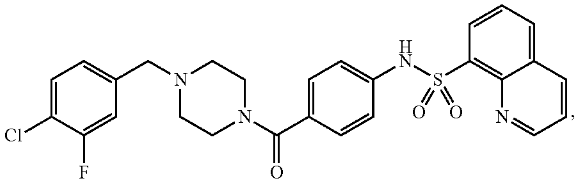,
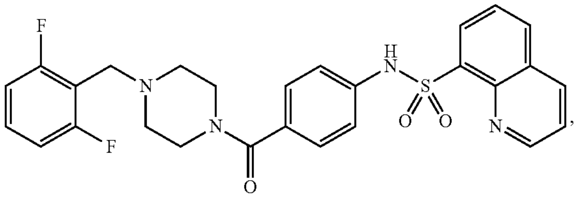,
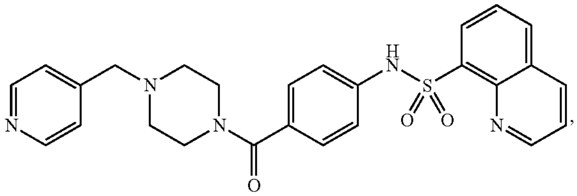,
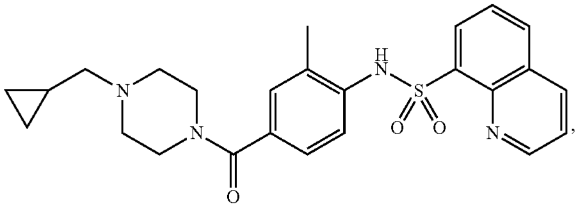,
-continued
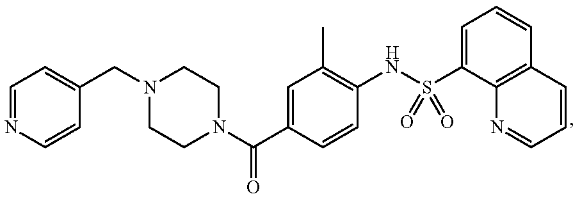,
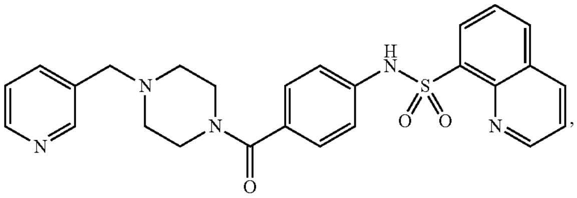,
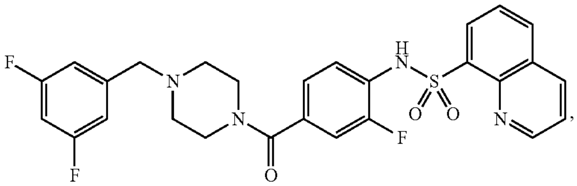,
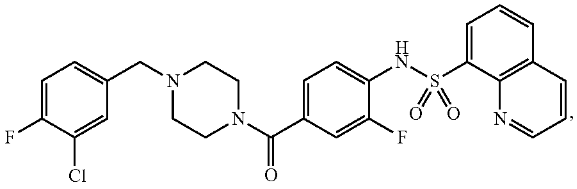,
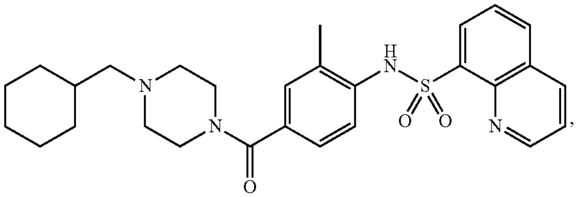,
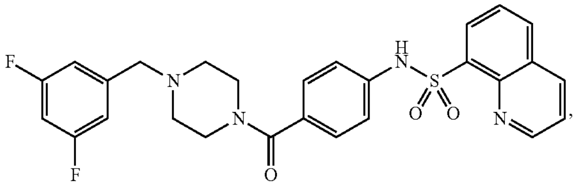,
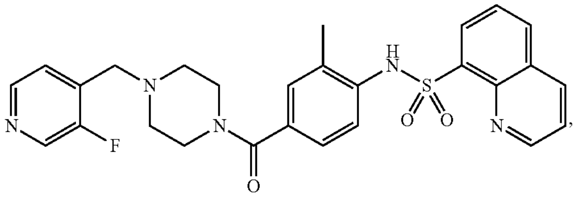,
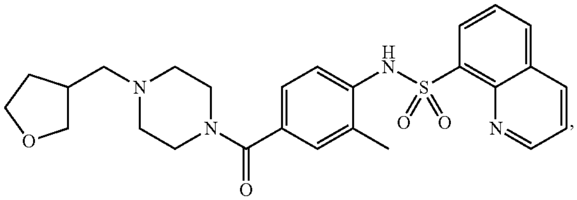, -continued

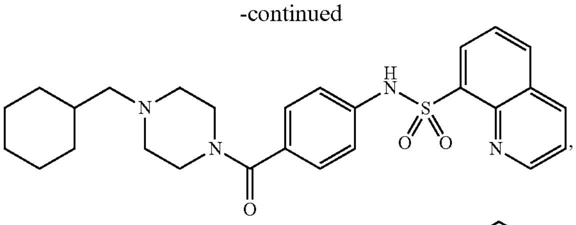

,

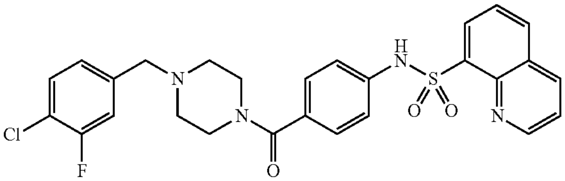

,

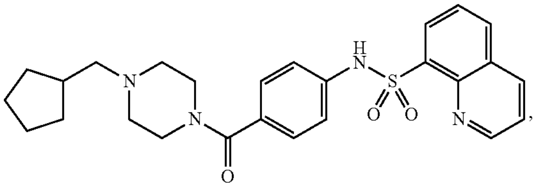

, and

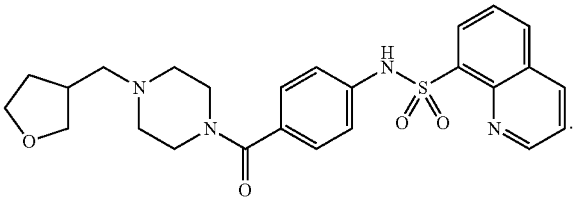

.

30. A method of treating a disorder selected from thalassemia, hereditary spherocytosis, hereditary elliptocytosis, abetalipoproteinemia or Bassen-Kornzweig syndrome, paroxysmal nocturnal hemoglobinuria, acquired hemolytic anemia, and anemia of chronic diseases in a subject in need thereof, comprising administering to the subject a therapeutically effective amount of a compound of formula I or a pharmaceutically acceptable salt thereof, wherein:

(I)

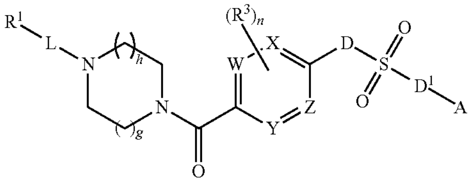

W, X, Y and Z are each independently selected from CH or N;

D and $D^1$ are each independently selected from a bond and $NR^b$;

A is optionally substituted aryl or optionally substituted heteroaryl;

L is a bond, —C(O)—, $—(CR^cR^c)_m—$, —OC(O)—, $—(CR^cR^c)_m—OC(O)—$, $—(CR^cR^c)_m—C(O)—$, $—NR^bC(S)—$, or $—NR^bC(O)—$ (wherein the point of the attachment to $R^1$ is on the left-hand side);

$R^1$ is selected from alkyl, cycloalkyl, aryl, heteroaryl, and heterocyclyl; each of which is substituted with 0-5 occurrences of $R^d$;

each $R^3$ is independently selected from halo, haloalkyl, alkyl, hydroxyl and $—OR^a$, or two adjacent $R^3$ taken together with the carbon atoms to which they are attached form an optionally substituted heterocyclyl;

each $R^a$ is independently selected from alkyl, acyl, hydroxyalkyl and haloalkyl;

each $R^b$ is independently selected from hydrogen and alkyl;

each $R^c$ is independently selected from hydrogen, halo, alkyl, alkoxy and halo alkoxy or two $R^c$ taken together with the carbon atoms to which they are attached form an optionally substituted cycloalkyl;

each $R^d$ is independently selected from halo, haloalkyl, haloalkoxy, alkyl, alkynyl, nitro, cyano, hydroxyl, $—C(O)R^a$, $—OC(O)R^a$, $—C(O)OR^a$, $—SR^a$, $—NR^aR^b$ and $—OR^a$, or two $R^d$ taken together with the carbon atoms to which they are attached form an optionally substituted heterocyclyl;

n is 0, 1, or 2;

m is 1, 2 or 3;

h is 0, 1, 2; and g is 0, 1 or 2.

* * * * *